US010668149B2

(12) United States Patent
Doshi et al.

(10) Patent No.: US 10,668,149 B2
(45) Date of Patent: Jun. 2, 2020

(54) COMBINATION THERAPIES FOR HEME MALIGNANCIES WITH ANTI-CD38 ANTIBODIES AND SURVIVIN INHIBITORS

(71) Applicant: Janssen Biotech, Inc., Horsham, PA (US)

(72) Inventors: Parul Doshi, Chester Springs, PA (US); Henk M. Lokhorst, De Boelelaan (NL); Tuna Mutis, De Boelelaan (NL)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/189,577

(22) Filed: Jun. 22, 2016

(65) Prior Publication Data

US 2016/0367663 A1    Dec. 22, 2016

Related U.S. Application Data

(60) Provisional application No. 62/182,699, filed on Jun. 22, 2015, provisional application No. 62/319,036, filed on Apr. 6, 2016.

(51) Int. Cl.
| | |
|---|---|
| *A61K 39/395* | (2006.01) |
| *A61K 9/00* | (2006.01) |
| *C07K 16/28* | (2006.01) |
| *A61K 31/497* | (2006.01) |
| *A61K 38/47* | (2006.01) |
| *A61K 39/00* | (2006.01) |

(52) U.S. Cl.
CPC ........ *A61K 39/3955* (2013.01); *A61K 9/0019* (2013.01); *A61K 31/497* (2013.01); *A61K 38/47* (2013.01); *C07K 16/2896* (2013.01); *A61K 2039/505* (2013.01); *C12Y 302/01035* (2013.01)

(58) Field of Classification Search
None
See application file for complete search history.

(56) References Cited

U.S. PATENT DOCUMENTS

| | | | |
|---|---|---|---|
| 6,737,056 B1 | 5/2004 | Presta | |
| 7,183,387 B1 | 2/2007 | Presta | |
| 7,223,397 B1 | 5/2007 | Rosenblum et al. | |
| 7,829,673 B2 * | 11/2010 | De Weers | G01N 33/566 530/387.1 |
| 7,829,693 B2 | 11/2010 | Kreutzer et al. | |
| 8,088,896 B2 | 1/2012 | Tesar et al. | |
| 8,153,765 B2 | 4/2012 | Park et al. | |
| 9,040,050 B2 | 5/2015 | Van De Winkel | |
| 9,603,927 B2 | 3/2017 | Doshi | |
| 9,732,154 B2 | 8/2017 | Doshi | |
| 10,385,135 B2 | 8/2019 | Jansson et al. | |
| 10,556,961 B2 | 2/2020 | Doshi | |
| 10,604,580 B2 | 3/2020 | Lokhorst | |
| 2004/0141982 A1 | 7/2004 | Lust et al. | |
| 2004/0268425 A1 | 12/2004 | Bookbinder et al. | |
| 2006/0257397 A1 | 11/2006 | Throsby | |
| 2007/0148178 A1 | 6/2007 | Fyfe et al. | |
| 2008/0063642 A1 | 3/2008 | Adelman et al. | |
| 2008/0166344 A1 | 7/2008 | Nakahara et al. | |
| 2009/0076249 A1 | 3/2009 | Deweers et al. | |
| 2009/0148449 A1 | 6/2009 | de Weers | |
| 2009/0304687 A1 | 12/2009 | Drachman | |
| 2009/0304710 A1 * | 12/2009 | Park ................... A61K 47/6867 424/158.1 |
| 2010/0068136 A1 | 3/2010 | Hansen | |
| 2010/0092489 A1 | 4/2010 | van de Winkel et al. | |
| 2010/0285004 A1 | 11/2010 | Tesar et al. | |
| 2011/0044977 A1 * | 2/2011 | Adler ................... A61K 9/0019 424/133.1 |
| 2011/0044997 A1 | 2/2011 | Adler et al. | |
| 2011/0066111 A1 | 3/2011 | Teschner et al. | |
| 2011/0099647 A1 | 4/2011 | De Weers et al. | |
| 2011/0293606 A1 | 12/2011 | Lejeune | |
| 2011/0300157 A1 | 12/2011 | Devy et al. | |
| 2012/0201827 A1 | 8/2012 | Elias | |
| 2012/0219551 A1 | 8/2012 | Johnson et al. | |
| 2012/0231008 A1 | 9/2012 | Guo et al. | |
| 2012/0244110 A1 | 9/2012 | Chen et al. | |
| 2012/0258081 A1 | 10/2012 | Corringham et al. | |
| 2012/0259095 A1 | 10/2012 | Beliard et al. | |
| 2012/0295864 A1 | 11/2012 | Taube et al. | |
| 2013/0109593 A1 | 5/2013 | Hartmann et al. | |
| 2013/0137134 A1 | 5/2013 | Mordechai et al. | |
| 2013/0209355 A1 | 8/2013 | De Weers et al. | |
| 2013/0302400 A1 | 11/2013 | Maneval et al. | |
| 2013/0309250 A1 | 11/2013 | Cogswell et al. | |
| 2013/0323247 A1 | 12/2013 | Zugmaier et al. | |
| 2014/0099254 A1 | 4/2014 | Chang et al. | |
| 2014/0155584 A1 | 6/2014 | Elias et al. | |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

Matas-Cespedes et al, Blood 2012, 120:3935.*
Weers et al. J. Immunol. 2011, 186:1840-1848.*
Kita et al., Leukemia Research, 2011, 35:787-792.*
Wagner et al., Blood, 2011, 118:137.*
Lu et al., The AAPS Journal 2006, 8(3): E466-E478.*
Haart et al., Haematologica, Aug. 2016, 101(8):e339-42, Epub: May 5, 2016.*
Aarhust, et al., "Adp-ribosyl Cyclase and CD38 Catalyze the Synthesis of a Calcium mobilizing Metabolite from NADP+," The Journal of Biological Chemistry, 270(51): 30327-30333 (1995).
Adriouch et al., "Extracellular NAD+: a danger signal hindering regulatory T cells," Microbes and Infection, 14:1284-1292 (2012).
Arican, et al., "Philadelphia chromosome (+) T-cell accute lymphoblastic leukaemia after renal transplantation," Nephrol Dial Transplant, vol. 14, No. 8, pp. 2054-2055, 1999.

(Continued)

*Primary Examiner* — Hong Sang
(74) *Attorney, Agent, or Firm* — Hamilton, Brook, Smith & Reynolds, P.C.

(57) ABSTRACT

The present invention relates to combination therapies for heme malignancies with anti-CD38 antibodies and survivin inhibitors.

6 Claims, 10 Drawing Sheets

Specification includes a Sequence Listing.

(56) References Cited

U.S. PATENT DOCUMENTS

| | | |
|---|---|---|
| 2014/0248238 A1 | 9/2014 | Wilson et al. |
| 2014/0271644 A1 | 9/2014 | Elias et al. |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1 | 8/2015 | Van De Winkel |
| 2015/0246123 A1 | 9/2015 | Doshi |
| 2015/0246975 A1 | 9/2015 | Doshi |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer |
| 2019/0127479 A1 | 5/2019 | Ahmadi et al. |
| 2019/0144557 A1 | 5/2019 | Ahmadi et al. |
| 2019/0233533 A1 | 8/2019 | Otten |
| 2019/0330363 A1 | 10/2019 | Janssen et al. |
| 2020/0002433 A1 | 1/2020 | Jansson et al. |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 | 12/2013 |
| EP | 2 561 868 A1 | 2/2013 |
| EP | 2567976 A2 | 3/2013 |
| JP | 2010-504363 A | 2/2010 |
| JP | 2014-509837 A | 4/2014 |
| NZ | 576122 A | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 01/97844 A1 | 12/2001 |
| WO | WO 02/06347 A1 | 1/2002 |
| WO | WO 02/32288 A2 | 4/2002 |
| WO | 2003/106498 A2 | 12/2003 |
| WO | WO 2004/058288 A1 | 7/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | 2008/073160 A2 | 6/2008 |
| WO | WO 2008/150530 A2 | 12/2008 |
| WO | WO 2009/062054 A1 | 5/2009 |
| WO | WO 2009/118142 A1 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2011/154453 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2014/048921 A1 | 4/2014 |
| WO | 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |
| WO | WO 2015/066450 A1 | 7/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | 2016/187546 A1 | 11/2016 |
| WO | WO 2016/209921 A1 | 12/2016 |
| WO | WO 2016/210223 A1 | 12/2016 |
| WO | WO 2017/079150 A1 | 5/2017 |
| WO | WO 2018/002181 A1 | 1/2018 |
| WO | 2019/089832 A1 | 5/2019 |

OTHER PUBLICATIONS

Armitage et al., "Long-Term Remission Durability and Functional Status of Patients Treated for Diffuse Histiocytic Lymphoma with the CHOP Regimen," J. Clin. Oncol. 2:898-902, 1984.

Arthur, "Innovations in subcutaneous infusions," J. Infus. Nurs. 38(3); 179-87; Abstract. p. 180, col. 2., Jun. 2015.

Bachireddy, et al., "Haematological Malignancies: at the Forefront of Immunotherapeutic 1-23, 50-58, 65-68, 75-77 Innovation," Nature Reviews Cancer, vol. 15, pp. 201-215, Apr. 1, 2015 (Apr. 1, 2015).

Blankestijn, et al., "Could daratumumab be used to treat severe allergy?," Journal of Allergy and Clinical Immunology, Elsevier, Amsterdam, NL, vol. 139, No. 5, p. 1677, Jan. 19, 2017.

Brown, et al., "Tolerance of single, but not multiple, amino acid replacements in antibody VH CDR 2: a means of minimizing B cell wastage from somatic hypermutation?" The Journal of Immunology, 156: 3285-3291 (1996).

Carter et al., "Identification and validation of cell surface antigens for antibody targeting in oncology," Endocrine-Related Cancer, vol. 11, pp. 659-687, 2004.

Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCTO2519452, Jun. 15, 2018.

Chari A. et al., "Subcutaneous delivery of daratumumab in patients (pts) with relapsed or refractory multiple myeloma (RRMM): PAVO, an openlabel, multicenter, dose escalation phase 1b study," ASH Annual Meeting ANZMAP Multiple Myeloma Highlights 2017.

Chen, et al., "Selection and Analysis of an Optimized Anti-VEGF Antibody: Crystal Structure of an Affinity-matured Fab in Complex with Antigen," Journal of Molecular Biology, 293: 865-881 (1999).

Cheson et al., "Revised Response Criteria for Malignant Lymphoma," Journal of Clinical Oncology, vol. 25, No. 5, 579-586 (Feb. 10, 2007).

Chou, et al., "Drug Combination Studies and their Synergy Quantification Using the Chou-Talalay Method," Cancer Research, 70(2): 440-446 (2010).

Colman, "Effects of amino acid sequence changes on antibody-antigen interactions," A Structural View of Immune Recognition by Antibodies, Biomolecular Research Institute, 33-36, Res Immunol.;145(1):33-6, Jan. 1994.

Cotner, et al., "Human T Cell Proteins Recognized by Rabbit Heteroantisera and Monoclonal Antibodies," International Journal of Immunopharmaceuticals, 3(3): 255-268 (1981).

Davies, et al., "Affinity improvement of single antibody VH domains: residues in all three hypervariable regions affect antigen binding," Immunotechnology, 2: 169-179 (1996).

(56) References Cited

OTHER PUBLICATIONS

Davis, et al., "Transgenic mice as a source of fully human antibodies for the treatment of cancer," Cancer and Metastasis Reviews, 18: 421-425 (1999).
Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research., vol. 20, No. 17, pp. 4574-4583, Sep. 1, 2014.
Dennis, "Off by a Whisker," Nature, 442 (17): 749-741 (2006).
DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).
De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (2011).
De Weers, M. et al., "Humax-CD38, a New Human CD38 Monoclonal Antibody, Effectively Mediates Killing of Multiple Myeloma and Plasma Cell Leukemia Cells," abstract, Submitted for the 16th European Congress of Immunology—ECI2006. Sep. 6-9, 2006—Paris, France.
De Weers et al., "HuMax-CD38, a new human CD38 monoclonal antibody, effectively mediates killing of multiple myeloma and plasma cell leukemia cells," The 23rd International Conference on Advances in the Application of Monoclonal Antibodies in Clinical Oncology, Jun. 26-28, 2006, Royal Myconian Resort & Thalasso Spa Center, Mykonos, Greece (Abstract).
Dos Santos, et al., Anti-Leukemic Activity of Daratumumba in Acute Myeloid Leukemia Cells and Patient-Derived Xenografts, Blood, vol. 124, Abstract 2312, 2014.
Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).
Ellis, et al., "Engineered Anti-CD38 Monoclonal Antibodies for Immunotherapy of Multiple Myeloma," The Journal of Immunology, 155: 925-937 (1995).
Engert, et al., "A Phase-I Study of an Anti-CD25 Ricin A-Chain Immunotoxin (RFT5-SMPT-dgA) in Patients with Refractory Hodgkin's Lymphoma," Blood, 99(2): 403-410 (1997).
Ferrero, et al., Characterization and phylogenetic epitope mapping of CD38 ADPR cyclase in the cynomolgus macaque, BMC Immunology, 5(21): 1-13 (2004).
Field-Smith, "Bortezomid (Velcade™) in the treatment of multiple myeloma," Therapeutic and Clinical Risk Management, 2(3): 271-279 (2006).
Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, 2001.
Franco, et al., "The transmembrane glycoprotein CD38 is a catalytically active transporter responsible for generation and influx of the second messenger cyclic ADP-ribose across membranes," FASEB Journal, 12: 1507-1520 (1998).
Fujimori, et al., "A Modeling Analysis of Monoclonal Antibody Percolation Though Tumors: A Binding-Site Barrier," Journal of Nucleic Medicine, 31: 119-1198 (1990).
Funaro et al., "CD38 Functions Are Regulated Through an Internalization Step," Journal of Immunology, 160: 2238-2247 (1998).
Funaro, et al., "Human CD38: a versatile leukocyte molecule with emerging clinical prospectives," Fundamental and Clinical Immunology, 3(3): 101-113 (1995).
Funaro, et al., "Identification and characterization of an active soluble form of human CD38 in normal and pathological fluids," International Immunology, 8(11): 1643-1650 (1998).
Funaro, et al., "Involvement of the Multilineage CD38 Molecule in a Unique Pathway of Cell Activation and Proliferation," The Journal of Immunology, 145: 2390-2396 (1990).
Gallo, et al., "The human immunoglobulin loci introduced into mice: V(D) and J gene segment usage similar to that of adult humans," European Journal of Immunology, 30: 534-540 (2000).
Genmab "Humanx-CD38 Effective in Preclinical Studies," Genmab A/S, Stock Exchange Release 57/2005.
Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status_010513_uk.pdf, May 1, 2013.
George, et al., "Differential Effects of Anti-β2-Glycoprotein I Antibodies on Endothelial Cells and on the Manifestations of Experimental Antiphospholipid Syndrome," Circulation, 97: 900-906 (1998).
Goldmacher, et al., "Anti-CD38-Blocked Ricin: An immunotoxin for the Treatment of Multiple Myeloma," The American Society of Hematology, 84(9): 3017-3025 (1994).
Goodwin, "Subcutaneous Daratumumab Potential Game Changer for Multiple Myeloma," Oncology Times, 2017 American Society of Hematology Annual Meeting, p. 49, (2017).
Gopalakrishnan, et al. "Daratumumab improves the anti-myeloma effect of newly emerging multidrug therapies," Blood and Lymphatic Cancer: Targets and Therapy, 3: 19-24 (2013).
Graeff, et al., "Enzymatic Synthesis and Characterizations of Cyclic GDp-ribose," The Journal of Biological Chemistry, 269(48): 30260-30267 (1994).
Green, "Antibody engineering via genetic engineering of the mouse: XenoMouse strains are a vehicle for the facile generation of therapeutic human monoclonal antibodies," Journal of Immunological Methods, 231: 11-23 (1999).
Green, et al., "Antigen-specific human monoclonal antibodies from mice engineered with hyman Ig heavy and light chain YACs," Nature Genetics, 7: 13-21 (1994).
Guse et al., "Regulation of calcium signaling in T lymphocytes by the second messenger cyclic ADP-ribose," Nature 398:70-73, 1999.
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor α-expressing Lymphoma Utilizing the α-emitting Radionuclide-eonjugated Monoclonal Antibody 212Bi-anti-Tac, Cancer Research, 54: 4362-4370 (1994).
Henry, et al., "the use of basiliximab in solid organ transplantation," Expert Opinion Pharmacotherapy, 3(10: 1657-1663 (2002).
Holm, et al., "Functional mapping and single chain construction of the anti-cytokeratin 8 monoclonal antibody TS1," Molecular Immunology, 44: 1075-1084 (2002).
Hoshino, et al., "Mapping of the Catalytic and Epitopic Sites of Human CD38/NAD+ Glycohydrolase to a Functional Domain in the Carboxyl Terminus1," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Jackson, et al., "Isolation of a cDNA Encoding the Human CD38 (T10) molecule, A Cell Surface Glycoprotein With an Unusual Discontinuous Pattern of Expression During Lymphocyte Differentiation," The Journal of Immunology, 144(7): 2811-2815 (1990).
Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) 41st Annual meeting, Jun. 4, 2018.

(56) References Cited

OTHER PUBLICATIONS

Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "The long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic, and cytogenetic features of 4 cases treated with chemotherapy and stem cell transplantation," Annals of Diagnostic Pathology, 10: 263-268 (2006).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Konopleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kupiec-Weglinski, "CD25-Targeted Therapy Revisited," Transplantation, 69(3): 38-330 (2000).
Lande, et al., "CD38 ligation plays a direct role in the induction of IL-1β, I-6, and IL-10 secretion in resting human monocytes," Cellular Immunology, 220: 30-38 (2002).
Laurie, et al., "The role of CD4+CD25+ immunoregulatory T cells in the induction of autoimmune gastritis," Immunology and Cell Biology, 89: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Leveque "Subcutaneous Administration of Anticancer Agents" Anticancer Research, Departments of Pharmacy, University Hospital, Strasbourg, France, vol. 34, pp. 1579-1586 (2014).
Lin, et al., "Structure-Function Relationships in Glucagon: Properties of Highly Purified Des-His1-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS One, vol. 9, No. 1, page Article No. e85571, Jan. 2014.
Lonberg, et al., "Antigen-specific human antibodies from mice comprising four distinct genetic modifications," Nature: 308: 856-859 (1994).
MacCallum, et al., "Antibody-antigen Interactions: Contact Analysis and Binding Site Topography," Journal of Molecular Biology, 262, 732-745 (1998).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Mills, et al., Characterization of Monoclonal Antibodies that Inhibit CD38 ADp-ribosyl Cyclase Activity, LSSURP HLB Program, Department of Pharmacology, University of Minnesota. (2007).
Mikhael et al., Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, 8 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma 14-17, 54 Correlates with Grade and Progression Free Survival, and is Associated with Intratumoral Expression of IL-1β, IL-8 and CXCL5," Journal for Immunotherapy of Cancer, vol. 2, p. 110-112, Nov. 6, 2014 (Nov. 6, 2014).
Nijhof, et al.,"Modulation of CD 38 Expression Levels on Multiple Myeloma Tumor Cells by All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor α Monoclonal Antibody," Cancer Research, 59: 328-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Parren, et al., "HuMax-CD38, a new human CD38 monoclonal antibody, effectively mediates killing of multiple myeloma and plasma cell leukemia cells," American Society of Hematology 47th annual meeting, Dec. 10-13, 2005, Atlanta, Georgia, USA (Abstract).
Parren, et al., HuMax-CD38, Myconos, Jun. 26, 2006.
Parren, et al., HuMax-CD38, Torino, Jun. 8-10, 2006.
Pascual, et al., "Anti-interleukin-2 receptor antibodies: basiliximab and daclizumab," Nephrology Dial. Transplant, 16: 1756-1760 (2001).
Paul, M.D., "Fundamental Immunology," Chapter 9, Raven Press, New York, 3rd ed., 29-295 (1993).
Peipp, et al., Fully Human CD38 Antibodies Efficiently Trigger ADCC and CDC of Multiple Myeloma Cell Lines and Primary Tumor Cells (Poster), Blood, vol. 106(11):944A, 47th Annual Meeting of the American Society of Hematology, 2005; published Nov. 16, 2005.
Peipp, et al., Fully Human CD38 Antibodies Efficiently Trigger ADCC and CDC of Multiple Myeloma and Plasma Cell Leukemia

(56) References Cited

OTHER PUBLICATIONS

Cells (Poster 2) Conference proceedings, poster presentation at the 2005 Annual Meeting of the American Society of Hematology, Dec. 12, 2005.
Peipp, et al., 47th Annual Meeting of the American Society of Hematology, Atlanta, GA, Dec. 10-13, 2005. (Meeting Abstract).
Peng, et al., "Oncolytic measles viruses displaying a single-chain antibody against CD38, a myeloma cell marker," Blood, 101, 2557-2562 (2003).
Richardson, et al., "Daratumumab," Drugs of the Future, 38(8): 545-554 (2013).
Rituxan Hycela Label, "Highlights of prescribing information. RITUXAN HYCELATM™ (rituximab and hyaluronidase human) injection, for subcutaneous use," 32 pages (Jun. 2017).
Salar et al., "Comparison of Subcutaneous Versus Intravenous Administration of Rituximab as Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanachez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
Shields, et al., "High Resolution mapping of the binding site on human IgG1 for FcγRi, FcγRII, FcγRIII, and FcRn and design of IgG1 variants with improved binding to the FcγR," J. Biol. Chem., vol. 276, No. 9, pp. 6591-6604, 2001.
Shubinsky, et al., "The CD38 Lymphocyte Differentiation Marker: New Insight into Its Ectoenzymatic Activity and Its Role as a Signal Transducer," Immunity, 7: 315-324 (1997).
Skeel, Handbook of Cancer Gliemotherapy, 3rd edition, Little, Brown & Co., pp. 343 (1991).
Tabernero, et al., "Adult precursor B-ALL with BCR/ABL gene rearrangements displays a unique immunophenotype based on the pattern of CD10, CD34, CD13, and CD38 expression," Leukemia, vol. 15, No. 3, pp. 406-414, 2001.
Terhorst, et al., "Biochemical Studies of the Human Thymocyte Cell-Surface Antigens T6, T9 and T10," Cell, 23: 771-780 (1981).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Vajdos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Van Bueren, et al., "Direct In Vitro Comparison of Daratumumab With Surrogate Analogs of Anti-CD38 Antibodies," New Evidence Apr. 2015Retrieved from the Internet: URL: Http:///www.newevidence. com/oncology/direct-in-vitro-comparison-of-daratumumab-with-surrogate-analogs-of-anti-cd38-antibodies> [retrieved on Feb. 3, 2016].
Van de Donk et al., "Monoclonal antibodies targeting CD38 in hematological malignancies and beyond authors' addresses," Immunological Reviews, vol. 270, pp. 95-112, Feb. 10, 2016.
Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).
Vorre, et al., "Multiple Daratumumab Abstracts to be Presented at EHA," ArrayDiagnostica, Abstract Only (2014).
Wagner, V., et al., "Preclinical Efficacy of Sepantronium Bromide (YM155) in multiple myeloma is conferred by down regulation of Mcl-1," Oncotarget, 5(21): 10237-10250 (2014).
Ye et al, "Abstract P240: Treg Increases HepG2 Cell Growth by RANK-RANKL pathway." 1-23, 50-58, 65-68, 75-77, Journal for Immunotherapy of Cancer, vol. 2, pp. 115-117, Nov. 6, 2014 (Nov. 6, 2014).
International Preliminary Report on Patentability dated May 5, 2018 for International Application No. PCT/US2016/59893, entitled "Subcutaneous Formulations of Anti-CD38 Antibodies and Their Uses".
International Search Report and Written Opinion dated Jan. 24, 2017 for International Application No. PCT/US2016/59893, entitled "Subcutaneous Formulations of Anti-CD38 Antibodies and Their Uses".
International Preliminary Report on Patentability dated Dec. 26, 2017 for International Application No. PCT/US2016/038702, entitled "Combination Therapies for Heme Malignancies With Anti-CD38 Antibodies and Survivin Inhibitors".
International Search Report and Written Opinion dated Nov. 29, 2016 for International Application No. PCT/US2016/038702, entitled "Combination Therapies for Heme Malignancies With Anti-CD38 Antibodies and Survivin Inhibitors".
International Preliminary Report on Patentability dated Mar. 14, 2017 for International Application No. PCT/US2015/048899, entitled "Combination Therapies With Anti-CD38 Antibodies".
International Search Report and Written Opinion dated Apr. 8, 2016 for International Application No. PCT/US2015/048899, entitled "Combination Therapies With Anti-CD38 Antibodies".
International Preliminary Report on Patentability dated Nov. 21, 2017 for International Application No. PCT/US2016/033544, entitled "Anti-CD38 Antibodies for Treatment of Light Chain Amyloidosis and Other CD38-Positive Hematological Malignancies".
International Search Report and Written Opinion dated Oct. 24, 2016 for International Application No. PCT/US2016/033544, entitled "Anti-CD38 Antibodies for Treatment of Light Chain Amyloidosis and Other CD38-Positive Hematological Malignancies".
International Preliminary Report on Patentability dated Jun. 6, 2016 for International Application No. PCT/US2015/063371, entitled "Anti-CD38 Antibodies for Treatment of Acute Myeloid Leukemia".
International Search Report and Written Opinion dated Feb. 19, 2016 for International Application No. PCT/US2015/063371, entitled "Anti-CD38 Antibodies For Treatment of Acute Myeloid Leukemia".
International Preliminary Report on Patentability dated Dec. 26, 2017 for International Application No. PCT/US2016/039165, entitled "Immune Modulation and Treatment of Solid Tumors With Antibodies That Specifically Bind CD38".
International Search Report and Written Opinion dated Oct. 14, 2016 for International Application No. PCT/US2016/039165, entitled "Immune Modulation and Treatment of Solid Tumors With Antibodies That Specifically Bind CD38".
International Preliminary Report on Patentability dated Sep. 6, 2016 for International Application No. PCT/US2015/017425, entitled "Anti-CD38 Antibodies For Treatment of Acute Lymphoblastic Leukemia".
International Search Report and Written Opinion dated Sep. 21, 2015 for International Application No. PCT/US2015/017425, entitled "Anti-CD38 Antibodies For Treatment of Acute Lymphoblastic Leukemia".
International Search Report and Written Opinion dated Sep. 25, 2017 for International Application No. PCT/EP2017/066063, entitled "Treatment of IgE-Mediated Diseases With Antibodies That Specifically Bind CD38".
International Preliminary Report on Patentability dated Sep. 6, 2016 for International Application No. PCT/US2015/017420, entitled "Combination Therapies With Anti-CD38 Antibodies".
International Search Report and Written Opinion dated Jul. 8, 2015 for International Application No. PCT/US2015/017420, entitled "Combination Therapies With Anti-CD38 Antibodies".
Intellectual Property Office of Singapore Written Opinion dated Apr. 17, 2018 for Application No. 11201701867S, entitled "Combination Therapies with Anti-CD38 Antibodies ".
Supplementary European Search Report dated Feb. 21, 2018 for European Application No. EP 15839752 , entitled "Combination Therapies with Anti-CD38 Antibodies".
ClinicalTrials.gov "Study of YM155 in Refractory Diffuse Large B-cell Lymphoma (DLBCL Subjects," Interventional Studies, U.S. National Library of Medicine, https://clinicaltrials.gov/ct2/show/record/NCT00498914, retrieved on Sep. 10, 2018.
Non Final Office Action for U.S. Appl. No. 15/340,290 dated Nov. 20, 2017.

(56) References Cited

OTHER PUBLICATIONS

Final Office Action for U.S. Appl. No. 15/340,290 dated May 16, 2018.
Non Final Office Action for U.S. Appl. No. 15/366,474 dated Nov. 20, 2017.
Final Office Action for U.S. Appl. No. 15/366,474 dated May 16, 2018.
Non Final Office Action for U.S. Appl. No. 14/847,428 dated Sep. 23, 2016.
Non Final Office Action for U.S. Appl. No. 15/386,391 dated Jun. 18, 2018.
Non Final Office Action for U.S. Appl. No. 15/160,476 dated Sep. 15, 2017.
Final Office Action for U.S. Appl. No. 15/160,476 dated Apr. 23, 2018.
Non Final Office Action for U.S. Appl. No. 14/956,890 dated Nov. 25, 2016.
Final Office Action for U.S. Appl. No. 14/956,890 dated Jul. 24, 2018.
Non Final Office Action for U.S. Appl. No. 15/340,214 dated May 16, 2018.
Non Final Office Action for U.S. Appl. No. 14/629,965 dated Dec. 21, 2015.
Final Office Action for U.S. Appl. No. 14/629,965 dated Apr. 29, 2016.
Notice of Allowance for U.S. Appl. No. 14/629,965 dated Apr. 13, 2017.
Non Final Office Action for U.S. Appl. No. 15/445,225 dated Jun. 29, 2018.
"A Prospective Phase II of Daratumumab in Previously Treated Systemic Light Chain (AL) Amyloidosis", published online at (http://cms.cws.net/content/beta.myelomasociety.org/files/2017ash/Roussel,%20Murielle-ASH2017.pdf (2017).
Agheli, A. et al., "A Rare Case of Primary Amyloidosis, Presenting with Severe Pulmonary Hypertension and Bilateral Pleural Effusion," Blood, vol. 106, p. 5100 (2005).
Chaulagain, C.P., et al., "How we Treat Systemic Light-Chain Amyloidosis," Clinical Advances in Hematology & Oncology, vol. 13; No. 5; 315-324 (2015).
Chillemi, A. et al., "Anti-CD38 Antibody Therapy: Windows of Opportunity Yielded by the Functional Characteristics of the Target Molecule," Molecular Medicine, vol. 19; 99-108 (2013).
Eldfors, et al., "Landscape of Mutations in Relapsed Acute Myeloid Leukemia," Blood, vol. 124 No. 21, p. 2367 (2014).
Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Dec. 2014).
Hu, Y. et al., "The Significance of Abnormal Plasma Cell Clone in Bone Marrow of Primary Systemic Light Chain Amyloidosis Patients," Blood, vol. 122; p. 5342 (2013).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Jackisch, et al., "Subcutaneous versus intravenous formulation of trastuzumab for HER2-positive early breast cancer: updated results from the phase III HannaH study," Annals of Oncology, vol. 26, pp. 320-325, 2015.
Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Kumar, S. et al., "Expression of CD52 on plasma cells in plasma cell proliferative disorders," Blood, vol. 102; No. 3; pp. 1075-1077 (2003).
Laubach, J.P., "Daratumumab granted breakthrough drug status," Expert Opinion, vol. 23; No. 4; 445-452 (2014).
Li, et al., "Creation of Patient Derived AML Xenografts Displaying Distinct Phenotypes and Geneotypes," Blood, vol. 122 No. 21, p. 5018 (2013).
Liu, Zhiqiang et al.: "Induction of Chemoresistance by All-Trans Retinoic Acid via a Noncanonical Signaling in Multiple Myeloma Cells", Biosis, Biosciences Information Service, Philadelphia, PA, US, (2014), Database accession No. PREV20140015197.
McCarthy, P.L., "Strategies for induction, autologous hematopoietic stem cell transplantation, consolidation, and maintenance for transplantation-eligible multiple myeloma patients", Hematology, vol. 2013, NI. 1, Dec. 1, 2013, pp. 496-503.
Nijhof, I.S. et al., "Combination of the anti-CD38 monoclonal antibody daratumumab and all-trans retinoic acid (Abstract in Proceedings of the AACR Special Conference on Hematologic Malignancies: Translating Discoveries to Novel Therapies). Clin Cancer Res, Sep. 20, 2014, vol. 21, No. 17 Suppl, pp. Abstract A12; Abstract".
Nijhof, I.S. et al.: "Modulation of CD38 Expression Levels on Multiple Myeloma Tumor Cells by All-Trans Retinoic Acid improves the Efficacy of the Anti-CD 38 Monoclonal Antibody Daratumumab," Blood, vol. 124; Abstract 2096 (2014).
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
"Phase 1/2 Dose Escalation and Efficacy Study of Anti-CD38 Monoclonal Antibody in Patients With Selected CD38+ Hematological Malignancies," First posted Mar. 10, 2010, ClinicalTrials.gov. identifier No. NCT01084252.
Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).
Sachchithanantham, S. et al., "Use of Plasma Cell Immunophenotype as Prognostic Markers in Patients with Systemic AL Amyloidosis," Blood, vol. 122; p. 3120 (2013).
Schonland, S., et al., "Detection and Charaterization of Plasma Cell and B Cell Clones in Patients with Systemic Light Chain Amyloidosis Using Flow Cytometry," Blood, vol. 124, p. 2068 (2014).
Shpilberg, et al., "Subcutaneous administration of rituximab (MabThera) and trastuzumab (Herceptin) using hyaluronidase," British Journal of Cancer, vol. 109, pp. 1556-1561, 2013.
Sonneveld, P. and Annemiek Broijl, "Treatment of Relapsed and Refractory Multiple Myeloma," Review Article, Leaders in Hematology, review series, Haematologica, 101(4):396-406 (2016).
Topalian, S.L., et al., "Immune Checkpoint Blockade: A Common Denominator Approach to Cancer Therapy," Cancer Cell, vol. 27; 450-461 (2015).
WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (Apr. 26, 2016).
Applicant Initiated Interview Summary for U.S. Appl. No. 15/366,474 dated Sep. 17, 2018.
Final Office Action for U.S. Appl. No. 15/445,225 dated Dec. 17, 2018.
Final Office Action for U.S. Appl. No. 15/651,333 dated Sep. 27, 2018.
Non Final Office Action for U.S. Appl. No. 15/340,290 dated Oct. 10, 2018.
Non Final Office Action for U.S. Appl. No. 15/366,474 dated Oct. 11, 2018.
Non Final Office Action for U.S. Appl. No. 15/160,476 dated Nov. 5, 2018.

(56) References Cited

OTHER PUBLICATIONS

Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).
Brand, F-X. et al., "Prospect for Anti-HER2 Receptor Therapy in Breast Cancer," AntiCancer Research, vol. 26; 463-470 (2006).
Dimopoulos, M.A. et al., "Daratumumab, plus lenalidomide and dexamethasone versus lenalidomide and dexamethasone in relapsed or refractory multiple myeloma: updated analysis of POLLUX," Haematologica, vol. 103; No. 12; 2088-2096 (2018).
Dimopoulos, M.A. et al., "Daratumumab, Lenalidomide, and Dexamethasone for Multiple Myemloma," The New England Journal of Medicine, vol. 375; No. 14; 1319-1331 (2016).
Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).
Krejcik, J. et al., Immunomodulatory Effects and Adaptive Immune Response to Daratumumab in Multiple Myeloma,: Blood, vol. 126; 3037; 7 pages (2015).
Lakshman, A. et al., "Efficacy of daratumumab-based therapies in patients with relapsed, refractory multiple myeloma treated outside of clinical trials," Am J. Hematol., vol. 92; 1146-1155 (2017).
Mauri, C. and Menon, M., "The expanding family of regulatory B cells," International Immunology, vol. 27; No. 10; 479-486 (2015).
Nijhof, I.S. et al., Preclinical Evidence for the Therapeutic Potential of CD38-Targeted Immuno-Chemotherapy in Multiple Myeloma Patients Refractory toLenalidomide and Bortezomib. Clin Cancer Res., vol. 21, No. 12, pp. 2802-2810 (2014).
Palumbo, A. et al., "Daratumumab, Bortezomib, and Dexamethasone for Multiple Myeloma," The New England Journal of Medicine, vol. 375; No. 8; 754-766 (2016).
Patton, D.T. et al., "The P13K p110δ Regulates Expression of CD38 on Regulatory T Cells," PLOS one, vol. 6; No. 3; e17359; 8 pages (2011).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
San-Miguel, J., "New approaches to myeloma treatment in 2017," EHA Learning Center; Abstract; 4 pages (2017).
Sher, T. et al., "First report of safety and efficacy of daratumumab in 2 cases of advanced immunoglobulin light chain amyloidosis," Blood, vol. 128; No. 15; 1987-1989 (2016).
Spencer, A. et al., "Daratumumab plus bortezomib and dexamethasone versus bortezomib and dexamethasone in relapsed or refractory multiple myeloma: updated analysis of Castor," Haematologica, vol. 103; No. 12; 2079-2087 (2018).
Strome, S. E. et al. "A Mechanistic Perspective of Monoclonal Antibodies in Cancer Therapy Beyond Target-Related Effects," The Oncologist, vol. 12; 1084-1095 (2007).
Talmadge, J.E. And Gabrilovich, D.I, "History of myeloid-derived suppressor cells," Nature Reviews, vol. 13; 739-752 (2013).
Usmani, S.Z. et al., "Efficacy of Daratumumab, Lenalidomide, and Dexamethasone Versus Lenalidomide and Dexamethasone in Relapsed or Refractory Multiple Patients with 1 to 3 Prior Lines of Therapy: Updated Analysis of Pollux," Blood, vol. 128; No. 22; 1151; 10 pages (2016).
Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).
International Search Report and Written Opinion dated Feb. 12, 2019 for International Application No. PCT/US2018/058561, entitles "Methods of Treating High Rist Multiple Myeloma".
Final Office Action for U.S. Appl. No. 15/386,391 dated Dec. 28, 2018.
Final Office Action for U.S. Appl. No. 14/956,890 dated Jan. 14, 2019.
Notice of Allowance for U.S. Appl. No. 15/651,333 dated Feb. 21, 2019.
Final Office Action for U.S. Appl. No. 15/340,290 dated Mar. 11, 2019.
Notice of Allowance for U.S. Appl. No. 15/386,391 dated Mar. 29, 2019.
Notice of Allowance for U.S. Appl. No. 15/340,290 dated May 22, 2019.
Notice of Allowance for U.S. Appl. No. 15/651,333 dated May 31, 2019.
Abdi, J. et al., "Drug resistance in multiple myeloma: latest findings and new concepts on molecular mechanisms," Oncotarget, vol. 4; No. 12; 2186-2207 (2013).
Chaulagain, C.P. and Comenzo, R.L., "New Insights and Modern Treatment of AL Amyloidosis," Curr Hematol Malig Rep, vol. 8; 291-298 (2013).
Chiarugi, A. et al., "The NAD metabolome—a key determinant of cancel cell biology," Nature Reviews, vol. 12; 741-752 (2012).
ClinicalTrials.gov, "Daratumumab in Combination with ATRA (DARA/ATRA)," Identifier: NCT02751255; First posted: Apr. 26, 2016.
Comenzo, R.L. et al., "Consensus guidelines for the conduct and reporting of clinical trials in systemic light-chain amyloidosis," Leukemia, vol. 26; 2317-2325 (2012).
Ettinger, R. et al., "Pathogenic mechanisms of IgE-mediated inflammation in self-destructive autoimmune responses," Autoimmunity, vol. 50; No. 1; 25-36 (2017).
Gupta, R. et al., "The Economic Impact of Childhood Food Allergy in the United States," JAMA Pediatrics, vol. 167; No. 11; 1026-1031 (2013).
Holgate, S.T., "New strategies with anti-IgE in allergic diseases," World Allergy Organization Journal, vol. 7; No. 17; 6 pages (2014).
Inaba, H. et al., "Acute lymphoblastic leukaemia," Lancet, vol. 381; 27 pages (2013).
Lepenies, B. and Jacobs, T., "The Role of Negative Costimulators During Parasitic Infections," Endocrine, Metabolic & Immune Disorders—Drug Targets, vol. 8; 279-288 (2008).
Manier, S. et al., "Bone Marrow Microenvironment in Multiple Myeloma Progession," Journal of Biomedicine and Biotechnology, vol. 2012; 5 pages (2012).
Merlini, G. and Bellotti, V., "Molecular Mechanisms of Amyloidosis," The New England Journal of Medicine, vol. 349; No. 6; 583-596 (2003).
Mills, E.N.C. et al., "The prevalence, cost and basis of food allergy across Europe," Allergy, vol. 62; 717-722 (2007).
Patel, J.P., "Prognostic Relevance of Integrated Genetic Profiling in Acute Myeloid Leukemia," The New England Journal of Medicine, vol. 366; No. 12; 1079-1089 (2012).
Sicherer, S.H. and Sampson, H.A., "Food allergy: Epidemiology, pathogenesis, diagnosis, and treatment," J. Allergy Clin Inmmunol, vol. 133; 291-307 (2014).
Swaika, A. et al., "Current state of anti-PD-L1 and anti-PD-1 agents in cancer therapy," Molecular Immunology, vol. 67; 4-17 (2015).
The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Wang, L. et al., "Vista, a novel mouse Ig superfamily ligand that negatively regulates T cell responses," J. Exp. Med., vol. 208; No. 3; 577-592 (2011).
Wei, W. et al., "Roles and mechanisms of the CD38/cyclic adenosine diphosphate ribose/Ca2+ signaling pathway," World Journal of Biological Chemistry, vol. 5; No. 1; 58-67 (2014).
Final Office Action for U.S. Appl. No. 15/160,476 dated Jun. 14, 2019.
Notice of Allowance for U.S. Appl. No. 15/445,225 dated Jul. 29, 2019.
Notice of Allowance for U.S. Appl. No. 15/386,391 dated Jul. 30, 2019.
Non-Final Office Action for U.S. Appl. No. 14/956,890 dated Jul. 30, 2019.
Notice of Allowance for U.S. Appl. No. 15/651,333 dated Oct. 9, 2019.

(56) References Cited

OTHER PUBLICATIONS

Notice of Allowance for U.S. Appl. No. 15/386,391 dated Nov. 18, 2019.
Notice of Allowance for U.S. Appl. No. 15/445,225 dated Dec. 4, 2019.
ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015.
ClinicalTrials.gov, "A Study to Evaluate Subcutaneous Daratumumab in Combination with Standard Multiple Myeloma Treatment Regimens," Identifier: NCT03412565, First Posted: Jan. 26, 2018 (16 pages).
Fujioka, Y. and Kurokawa, M., "Follicular lymphoma presenting with massive splenomegaly," International J Hematol, vol. 95; 3-4 (2012).
Kaufman, G.P. et al., "Daratumumab yields rapid and deep hematologic responses in patients with heavily pretreated AL amyloidosis," Blood, vol. 130; No. 7; 900-902 (2017).
Machida, H. et al., " Aggressive plasma cell leukemia with cleaved, multilobated and monocytoid nuclei," International Journal of Hematol., vol. 73; Suppl 1; 158; Abstract No. 411 (2002).
Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).
Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. P340 (2002).
Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).
Ryan, A. et al., "Potentiation of Anti-Myeloma Activity of Daratumumab with Combination of Cyclophosphamide, Lenalidomide or Bortezomib via a Tumor Secretory Response That Greatly Augments Macrophage-Induced ADCP," Annual Meeting at the Haematology Association of Ireland, Oct. 15, 2016; 20 pages.
Saito, M. et al., "A Case of Retroperitoneal Extramedullary Plasmacytoma," Acta Urol. Jpn., vol. 49; 735-739 (2003).
Usmani, S.Z. et al., "Open-Label, Multicenter, Dose Escalation Phase 1b Study to Assess the Subcutaneous Delivery of Daratumumab in Patients (pts) with Relapsed or Refractory Multiple Myeloma," Blood, vol. 128; No. 22; 1149 (2016).
Usmani, S.Z. et al., "Subcutaneous delivery of daratumumab in relapsed or refractory multiple myeloma," Blood, vol. 134; No. 8; 668-677 (2019).
International Preliminary Report on Patentability dated Jan. 10, 2019 for International Application No. PCT/EP2017/066063, entitled "Treatment of IgE-Mediated Diseases With Antibodies That Specifically Bind CD38".
Non Final Office Action for U.S. Appl. No. 15/160,476 dated Dec. 20, 2019.
Final Office Action for U.S. Appl. No. 14/956,890 dated Jan. 7, 2020.
Non-Final Office Action for U.S. Appl. No. 15/798,670 dated Jan. 22, 2020.
English translation of Office Action for JP Application No. 2016-554350, dated Nov. 27, 2018.

* cited by examiner

COMBINATION THERAPIES FOR HEME MALIGNANCIES WITH ANTI-CD38 ANTIBODIES AND SURVIVIN INHIBITORS

CROSS-REFERENCE TO RELATED APPLICATIONS

This application claims the benefit of U.S. Provisional Application Ser. No. 62/182,699, filed 22 Jun. 2015, and U.S. Provisional Application Ser. No. 62/319,036, filed 6 Apr. 2015, the entire contents of which are incorporated herein by reference.

FIELD OF THE INVENTION

The present invention relates to combination treatments for heme malignancies.

BACKGROUND OF THE INVENTION

Multiple Myeloma (MM) is a B cell malignancy characterized by the latent accumulation of secretory plasma cells in bone marrow with a low proliferative index and an extended life span. The disease ultimately attacks bones and bone marrow, resulting in multiple tumors and lesions throughout the skeletal system. Approximately 1% of all cancers, and slightly more than 10% of all hematologic malignancies, can be attributed to MM. Incidence of MM increases in the aging population, with the median age at time of diagnosis being about 61 years.

Currently available therapies for MM include chemotherapy regimens, stem cell transplantation, THALOMID® (thalidomide), REVLIMID® (lenalidomide), POMALYST® (pomalidomide), VELCADE® (bortezomib), KYPROLIS® (carfilzomib), FARADYK® (panobinostat), AREDIA® (pamidronate), and ZOMETA® (zoledronic acid). Current treatment protocols, which include a combination of chemotherapeutic agents such as vincristine, BCNU, melphalan, cyclophosphamide, adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Nevertheless, overall survival has only been slightly prolonged, and no evidence for a cure has been obtained. Ultimately, all MM patients relapse, even under maintenance therapy with interferon-alpha (IFN-α) alone or in combination with steroids.

Efficacy of the available drug treatment regimens for MM is limited by the low cell proliferation rate and development of drug resistance in up to 90% of patients. Chromosomal translocations, oncogene mutations, dysregulated signaling pathways such as anti-apoptotic and survival pathways and bone marrow niche been implicated to contribute to drug resistance in MM (for review, see Abdi et al., Oncotarget 4:2186-2207, 2013). The bone marrow (BM) niche is implicated in proliferation, survival, differentiation, migration, and drug resistance of the malignant plasma cells (Manier et al., J Biomed Biotechnol 2012; published online 2012 Oct. 3, doi:_10.1155/_2012/_157496).

CD38, a type II transmembrane glycoprotein is an attractive target for antibody therapeutics for various heme malignancies, including multiple myeloma. Anti-CD38 antibodies are described, for example, in Intl. Pat. Publ. No. WO2008/037257, Intl. Pat. Publ. No. WO2008/047242 and Intl. Pat. Publ. No. WO2007/042309, and are being evaluated in clinical settings for their efficacy in multiple myeloma and other heme malignancies.

SUMMARY OF THE INVENTION

The invention provides for a method of treating a subject having a CD38-positive hematological malignancy, comprising administering to the subject in need thereof an anti-CD38 antibody and a survivin inhibitor for a time sufficient to treat the CD38-positive hematological malignancy.

DETAILED DESCRIPTION OF THE INVENTION

Figure 1A:
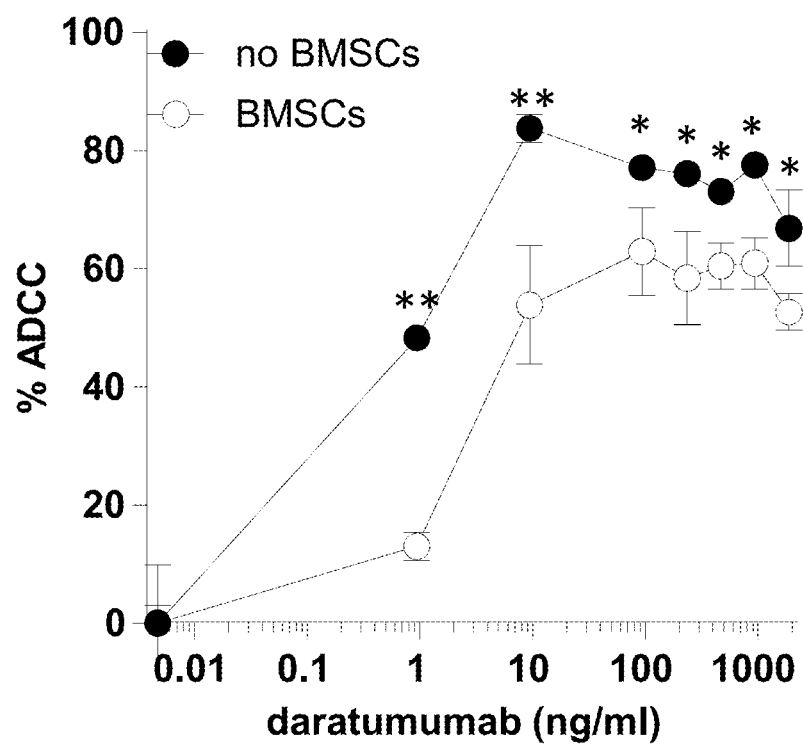
FIG. 1A. Bone Marrow stromal cells (BMSCs) mediate protection against multiple myeloma (MM) cell killing by ADCC induced by anti-CD38 antibody daratumumab in MM cell lines. Luciferase transduced $CD38^+$ UM9 MM cells were cultured in the presence or absence of healthy donor BMSCs (HD-BMSCs) for 16 hours prior to incubation with serial concentrations of daratumumab and HD-PBMCs at a PBMC:MM cell ratio of 30:1. MM cell viability was determined after 4 hours by bioluminescence imaging (BLI). Percent (%) ADCC was calculated relative to the cell viability without daratumumab. Error bars indicate the standard error of the mean (SEM) of triplicate measurements. The data are representative for 3 independent experiments. The differences between cultures with or without BMSCs were tested with an unpaired t test *=$p<0.05$.

"CD38" refers to the human CD38 protein (synonyms: ADP-ribosyl cyclase 1, cADPr hydrolase 1, cyclic ADP-ribose hydrolase 1). Human CD38 has an amino acid sequence as shown in SEQ ID NO: 1. it is well known that CD38 is a single pass type II membrane protein with amino acid residues 1-21 representing the cytosolic domain, amino acid residues 22-42 representing the transmembrane domain, and residues 43-300 representing the extracellular domain of CD38.

The term "antibodies" as used herein is meant in a broad sense and includes immunoglobulin molecules including, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CHI domains; a F(ab)$_2$ fragment, a bivalent fragment comprising two Fab fragments linked by a disulfide bridge at the hinge region; a Fd fragment consisting of the VH and CHI domains; a Fv fragment consisting of the VL and VH domains of a single arm of an antibody; a domain antibody (dAb) fragment (Ward et al., Nature 341:544-546, 1989), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

The phrase "isolated antibody" refers to an antibody or antibody fragment that is substantially free of other antibodies having different antigenic specificities (e.g., an isolated antibody specifically binding CD38 is substantially free of antibodies that specifically bind antigens other than human CD38). An isolated antibody that specifically binds CD38, however, can have cross-reactivity to other antigens, such as orthologs of human CD38, such as *Macaca fascicularis* (cy nomolgus) CD38. Moreover, an isolated antibody may be substantially free of other cellular material and/or chemicals.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3), and three in the VL (LCDR1, LCDR2, LCDR3) are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to for example naturally occurring somatic mutations or intentional introduction of substitutions in the framework or antigen binding sites. Typically, a "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, as described in, for example, Shi et al., J Mol Biol 397:385-96, 2010 and Intl. Pat. Publ. No. WO2009/085462). Antibodies in which antigen binding sites are derived from a non-human species are not included in the definition of "human antibody".

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

"Recombinant antibody" includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange.

"Monoclonal antibody" refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes. "Monoclonal antibody" therefore refers to an antibody population with single amino acid composition in each heavy and each light chain, except for possible well known alterations such as removal of C-terminal lysine from the antibody heavy chain Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" refers to a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions or deletions.

"In combination with" means that two or more therapeutics can be administered to a subject together in a mixture, concurrently as single agents or sequentially as single agents in any order.

"Treat" or "treatment" refers to both therapeutic treatment and prophylactic or preventative measures, wherein the object is to prevent or slow down (lessen) an undesired physiological change or disorder, such as the development or spread of a tumor or tumor cells. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable and prolonging survival as compared to expected survival if not receiving treatment. Those in need of treatment include those already with the condition or disorder as well as those prone to have the condition or disorder or those in which the condition or disorder is to be prevented.

"Therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics that may decline or abate in association with resistance include, for example, improved well-being of the patient, reduction of a tumor burden, arrested or slowed growth of a tumor, and/or absence of metastasis of cancer cells to other locations in the body.

"Synergy", "synergism" or "synergistic" mean more than the expected additive effect of a combination.

"Inhibits growth" (e.g., referring to cells, such as tumor cells) refers to a measurable decrease in the cell growth in vitro or in vivo when contacted with a therapeutic or a combination or therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100% Inhibition of cell growth can occur by a variety of mechanisms, for example by ADCC, apoptosis, necrosis, or by inhibition of cell proliferation.

"Subject" includes any human or nonhuman animal "Nonhuman animal" includes all vertebrates, e.g., mammals and non-mammals, such as nonhuman primates, sheep, dogs, cats, horses, cows chickens, amphibians, reptiles, etc. The terms "subject" and "patient" are used interchangeably herein.

"Survivin" as used herein refers to the survivin protein having the amino acid sequence shown in SEQ ID NO: 22. Survivin is a member of the inhibitor of apoptosis (IAP) family. Survivin is a dual functional protein acting as an apoptosis inhibitor and cell cycle regulator. Overexpression of survivin is observed in human malignancies and positively correlates with poor prognosis, tumor recurrence, and therapeutic resistance (Liu et al., Cancer Biol. Ther., 7:1053-1060, 2008; Mita et al., Clin Cancer Res., 14:5000-5005, 2008).

SEQ ID NO: 22
MGAPTLPPAWQPFLKDHRISTFKNWPFLEGCACTPERMAEAGFIHCPT

ENEPDLAQCFFCFKELEGWEPDDDPIEEHKKHSSGCAFLSVKKQFEEL

TLGEFLKLDRERAKNKIAKETNNKKKEFEETAEKVRRAIEQLAAMD

"Survivin inhibitor" refers to a molecule that inhibits, antagonizes, reduces or suppresses survivin activity; e.g., a molecule that inhibits the anti-apoptotic activity of survivin in a cell. Survivin inhibitor may inhibit the anti-apoptotic activity of survivin by about 20%, 30%, 40%, 50%, 60%, 70%, 80%, 90%, 99%, or 100%. Survivin inhibitors may be a small molecule, peptide, a vaccine, a polynucleotide, DNA or RNA molecule.

The present invention is based, at least in part, on the finding that bone marrow stromal cells (BMSC) residing in the BM niche protect MM cells against antibody-induced ADCC at least in part by upregulating survivin, and that survivin inhibitors improve antibody-mediated ADCC of MM cells and abrogate ADCC resistance induced by BMSCs. BMSCs have been shown to protect MM cells from cytotoxic T-lymphocyte (CTL)-dependent lysis via cell adhesion-mediated immune resistance, and survivin has been found to be upregulated in the lysis-resistant MM cells (de Haart et al., Clin Cance Res 19:5591-5601, 2013).

The invention provides for a method of treating a subject having a CD38-positive hematological malignancy, comprising administering to the subject in need thereof an anti-CD38 antibody and a survivin inhibitor for a time sufficient to treat the CD38-positive hematological malignancy.

The invention also provides for a method of inhibiting growth or proliferation of multiple myeloma cells in a subject, comprising administering an anti-CD38 antibody and a survivin inhibitor to the subject in need thereof for a time sufficient to inhibit growth or proliferation of multiple myeloma cells.

"CD38-positive hematological malignancy" refers to a hematological malignancy characterized by the presence of tumor cells expressing CD38, including leukemias, lymphomas and myeloma. Exemplary such CD38-positive hematological malignancies are precursor B-cell lymphoblastic leukemia/lymphoma and B-cell non-Hodgkin's lymphoma, acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma (MM), plasma cell leukemia, post-transplant lymphoproliferative disorder, Waldenstrom's macroglobulinemia, plasma cell leukemias and anaplastic large-cell lymphoma (ALCL).

CD38 is expressed in a variety of malignant hematological diseases, including multiple myeloma, leukemias and lymphomas, such as B-cell chronic lymphocytic leukemia, T- and B-cell acute lymphocytic leukemia, Waldenstrom's macroglobulinemia, primary systemic amyloidosis, mantle-cell lymphoma, pro-lymphocytic/myelocytic leukemia, acute myeloid leukemia, chronic myeloid leukemia, follicular lymphoma, Burkitt's lymphoma, large granular lymphocytic (LGL) leukemia, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression could be involved include, e.g., bronchoepithelial carcinomas of the lung, breast cancer (evolving from malignant proliferation of epithelial lining in ducts and lobules of the breast), pancreatic tumors, evolving from the β-cells (insulinomas), tumors evolving from epithelium in the gut (e.g. adenocarcinoma and squamous cell carcinoma), carcinoma in the prostate gland, and seminomas in testis and ovarian cancers. In the central nervous system, neuroblastomas express CD38.

In some embodiments, the CD38-positive hematological malignancy is multiple myeloma (MM), acute lymphoblastic leukemia (ALL), non-Hodgkin's lymphoma (NHL), diffuse large B-cell lymphoma (DLBCL), Burkitt's lymphoma (BL), follicular lymphoma (FL), mantle-cell lymphoma (MCL), acute myeloid leukemia (AML) or chronic lymphocytic leukemia (CLL).

In some embodiments, the CD38-positive hematological malignancy is MM.

In some embodiments, the CD38-positive hematological malignancy is ALL.

In some embodiments, the CD38-positive hematological malignancy is NHL.

In some embodiments, the CD38-positive hematological malignancy is DLBCL.

In some embodiments, the CD38-positive hematological malignancy is BL.

In some embodiments, the CD38-positive hematological malignancy is FL.

In some embodiments, the CD38-positive hematological malignancy is MCL.

In some embodiments, the CD38-positive hematological malignancy is AML.

In some embodiments, the CD38-positive hematological malignancy is CLL.

In some embodiments, the CD38-positive hematological malignancy is a plasma cell disease.

In some embodiments, the plasma cell disease is light chain amyloidosis (AL), multiple myeloma (MM) or Waldenstrom's macroglobulinemia.

In some embodiments, the plasma cell disease is AL.

In some embodiments, the plasma cell disease is MM.

In some embodiments, the plasma cell disease is Waldenstrom's macroglobulinemia.

Examples of B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

In one embodiment, the disorder involving cells expressing CD38 is Hodgkin's lymphoma.

Other examples of disorders involving cells expressing CD38 include malignancies derived from T and NK cells including mature T cell and NK cell neoplasms including T-cell prolymphocytic leukemia, T-cell large granular lymphocytic leukemia, aggressive NK cell leukemia, adult T-cell leukemia/lymphoma, extranodal NK/T cell lymphoma, nasal type, 78 enteropathy-type T-cell lymphoma, hepatosplenic T-cell lymphoma, subcutaneous panniculitis-like T-cell lymphoma, blastic NK cell lymphoma, Mycosis Fungoides/Sezary Syndrome, primary cutaneous CD30 positive T-cell lymphoproliferative disorders (primary cutaneous anaplastic large cell lymphoma C-ALCL, lymphomatoid papulosis, borderline lesions), angioimmunoblastic T-cell lymphoma, peripheral T-cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

Any anti-CD38 antibody may be used in the methods of the invention. The variable regions of the anti-CD38 antibodies may be obtained from existing anti-CD38 antibodies and optionally cloned as full length antibodies using standard methods. Exemplary antibody variable regions binding CD38 that may be used are described for example in Intl. Pat. Publ. Nos. WO05/103083, WO06/125640, WO07/042309, WO08/047242, WO12/092612, WO06/099875, and WO11/154453A1.

An exemplary anti-CD38 antibody that may be used is DARZALEX™ (daratumumab). DARZALEX™ (daratumumab) comprises a heavy chain variable region (VH) and a light chain variable region (VL) amino acid sequences as shown in SEQ ID NO: 4 and 5, respectively, a heavy chain complementarity determining region (HCDR) 1, a HCDR2 and a HCDR3 amino acid sequences as shown in SEQ ID NOs: 6, 7 and 8, respectively, and a light chain complementarity determining region (LCDR) 1, a LCDR2 and a LCDR3 amino acid sequences as shown in SEQ ID NOs: 9, 10 and 11, respectively, and is of IgG1/κ subtype. DARZALEX™ (daratumumab) heavy chain amino acid sequence is shown in SEQ ID NO: 12 and light chain amino acid sequence shown in SEQ ID NO: 13.

```
                                              SEQ ID NO: 1
MANCEFSPVSGDKPCCRLSRRAQLCLGVSILVLILVVVLAVVVPRWRQ

QWSGPGTTKRFPETVLARCVKYTEIHPEMRHVDCQSVWDAFKGAFISK

HPCNITEEDYQPLMKLGTQTVPCNKILLWSRIKDLAHQFTQVQRDMFT
```

-continued
LEDTLLGYLADDLTWCGEFNTSKINYQSCPDWRKDCSNNPVSVFWKTV

SRRFAEAACDVVHVMLNGSRSKIFDKNSTFGSVEVHNLQPEKVQTLEA

WVIHGGREDSRDLCQDPTIKELESIISKRNIQFSCKNIYRPDKFLQCV

KNPEDSSCTSEI

SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWV

SAISGSGGGTYYADSVKGRFTISRDNSKNTLYLQMNSLRAEDTAVYFC

AKDKILWFGEPVFDYWGQGTLVTVSS

SEQ ID NO: 5
EIVLTQSPATLSLSPGERATLSCRASQSVSSYLAWYQQKPGQAPRLLI

YDASNRATGIPARFSGSGSGTDFTLTISSLEPEDFAVYYCQQRSNWPP

TFGQGTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWV

SAISGSGGGTYYADSVKGRFTISRDNSKNTLYLQMNSLRAEDTAVYFC

AKDKILWFGEPVFDYWGQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPELL

GGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSV

MHEALHNHYTQKSLSLSPGK

SEQ ID NO: 13
EIVLTQSPATLSLSPGERATLSCRASQSVSSYLAWYQQKPGQAPRLLI

YDASNRATGIPARFSGSGSGTDFTLTISSLEPEDFAVYYCQQRSNWPP

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

Another exemplary anti-CD38 antibody that may be used is mAb003 comprising the VH and VL sequences of SEQ ID NOs: 14 and 15, respectively and described in U.S. Pat. No. 7,829,693.

SEQ ID NO: 14
QVQLVQSGAEVKKPGSSVKVSCKASGGTFSSYAFSWVRQAPGQGLEWM

GRVIPFLGIANSAQKFQGRVTITADKSTSTAYMDLSSLRSEDTAVYYC

ARDDIAALGPFDYWGQGTLVTVSSAS

SEQ ID NO: 15
DIQMTQSPSSLSASVGDRVTITCRASQGISSWLAWYQQKPEKAPKSLI

YAASSLQSGVPSRFSGSGSGTDFTLTISSLQPEDFATYYCQQYNSYPR

TFGQGTKVEIK

Another exemplary anti-CD38 antibody that may be used is mAb024 comprising the VH and VL sequences of SEQ ID NOs: 16 and 17, respectively and described in U.S. Pat. No. 7,829,693.

SEQ ID NO: 16
EVQLVQSGAEVKKPGESLKISCKGSGYSFSNYWIGWVRQMPGKGLEWM

GIIYPHDSDARYSPSFQGQVTFSADKSISTAYLQWSSLKASDTAMYYC

ARHVGWGSRYWYFDLWGRGTLVTVSS

SEQ ID NO: 17
EIVLTQSPATLSLSPGERATLSCRASQSVSSYLAWYQQKPGQAPRLLI

YDASNRATGIPARFSGSGSGTDFTLTISSLEPEDFAVYYCQQRSNWPP

TFGQGTKVEIK

Another exemplary anti-CD38 antibody that may be used is MOR-202 (MOR-03087) comprising the VH and VL sequences of SEQ ID NOs: 18 and 19, respectively and described in US. Pat. No. 8,088,896.

SEQ ID NO: 18
QVQLVESGGGLVQPGGSLRLSCAASGFTFSSYYMNWVRQAPGKGLEWV

SGISGDPSNTYYADSVKGRFTISRDNSKNTLYLQMNSLRAEDTAVYYC

ARDLPLVYTGFAYWGQGTLVTVSS

SEQ ID NO: 19
DIELTQPPSVSVAPGQTARISCSGDNLRHYYVYWYQQKPGQAPVLVIY

GDSKRPSGIPERFSGSNSGNTATLTISGTQAEDEADYYCQTYTGGASL

VFGGGTKLTVLGQ

Another exemplary anti-CD38 antibody that may be used is isatuximab, comprising the VH and VL sequences of SEQ ID NOs: 20 and 21, respectively, described in U.S. Pat. No. 8,153,765. The VH and the VL of isatuximab may be expressed as IgG1/κ.

SEQ ID NO: 20
QVQLVQSGAEVAKPGTSVKLSCKASGYTFTDYWMQWVKQRPGQGLEWI

GTIYPGDGDTGYAQKFQGKATLTADKSSKTVYMHLSSLASEDSAVYYC

ARGDYYGSNSLDYWGQGTSVTVSS

-continued

SEQ ID NO: 21
DIVMTQSHLSMSTSLGDPVSITCKASQDVSTVVAWYQQKPGQSPRRLI

YSASYRYIGVPDRFTGSGAGTDFTFTISSVQAEDLAVYYCQQHYSPPY

TFGGGTKLEIK

Anti-CD38 antibodies used in the methods of the invention may also be selected de novo from for example a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated for example from phage display libraries expressing antibody heavy and light chain variable regions as fusion proteins with bacteriophage pIX coat protein as described in Shi et al (2010) J. Mol. Biol. 397:385-96 and Intl. Pat. Publ. No. WO09/085462). The antibody libraries may be screened for binding to human CD38 extracellular domain and the obtained positive clones may be further characterized and the Fabs isolated from the clone lysates, and subsequently cloned as full length antibodies. Such phage display methods for isolating human antibodies are established in the art. See for example: U.S. Pat. Nos. 5,223,409; 5,403,484; and 5,571,698, 5,427,908, 5,580,717, 5,969,108, 6,172,197, 5,885,793; 6,521,404; 6,544,731; 6,555,313; 6,582,915 and 6,593,081.

The invention also provides for a method of treating a subject having a CD38-positive hematological malignancy, comprising administering to the subject in need thereof an anti-CD38 antibody that competes for binding to CD38 with an antibody comprising the VL of SEQ ID NO: 4 and the VL of SEQ ID NO: 5 and a survivin inhibitor for a time sufficient to treat the CD38-positive hematological malignancy.

The invention also provides for a method of treating a subject having multiple myeloma, comprising administering to the subject in need thereof an anti-CD38 antibody that competes for binding to CD38 with an antibody comprising the VH of SEQ ID NO: 4 and the VL of SEQ ID NO: 5 and a survivin inhibitor for a time sufficient to treat multiple myeloma.

The invention also provides for a method of treating a subject having a CD38-positive hematological malignancy, comprising administering to the subject in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1) and a survivin inhibitor for a time sufficient to treat the CD38-positive hematological malignancy.

The invention also provides for a method of treating a subject having multiple myeloma, comprising administering to the subject in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1). and a survivin inhibitor for a time sufficient to treat multiple myeloma.

In some embodiments, the anti-CD38 antibody comprises the HCDR1, the HCDR2 and the HCDR2 of SEQ ID NOs: 6, 7 and 8, respectively.

In some embodiments, the anti-CD38 antibody comprises the LCDR1, the LCDR2 and the LCDR3 of SEQ ID NOs: 9, 10 and 11, respectively.

In some embodiments, the anti-CD38 antibody comprises the HCDR1, the HCDR2, the HCDR3, the LCDR1, the LCDR2 and the LCDR3 of SEQ ID NOs: 6, 7, 8, 9, 10 and 11, respectively.

In some embodiments, the anti-CD38 antibody comprises the VL comprising an amino acid sequence that is 95%, 96%, 97%, 98%, 99% or 100% identical to that of SEQ ID NO: 4 and the VL comprising an amino acid sequence that is 95%, 96%, 97%, 98%, 99% or 100% identical to that of SEQ ID NO: 5.

In some embodiments, the anti-CD38 antibody comprises the VH of SEQ ID NO: 4 and the VL of SEQ ID NO: 5.

In some embodiments, the anti-CD38 antibody comprises the VH of SEQ ID NO: 14 and the VL of SEQ ID NO: 15.

In some embodiments, the anti-CD38 antibody comprises the VH of SEQ ID NO: 16 and the VL of SEQ ID NO: 17

In some embodiments, the anti-CD38 antibody comprises the VH of SEQ ID NO: 18 and the VL of SEQ ID NO: 19.

In some embodiments, the anti-CD38 antibody comprises the VH of SEQ ID NO: 20 and the VL of SEQ ID NO: 21.

Antibodies may be evaluated for their competition with a reference antibody, for example DARZALEX™ (daratumumab having the VH of SEQ ID NO: 4 and the VL of SEQ ID NO: 5 for binding to CD38 using well known in vitro methods. In an exemplary method, CHO cells recombinantly expressing CD38 may be incubated with unlabeled reference antibody for 15 min at 4° C., followed by incubation with an excess of fluorescently labeled test antibody for 45 min at 4° C. After washing in PBS/BSA, fluorescence may be measured by flow cytometry using standard methods. In another exemplary method, extracellular portion of human CD38 may be coated on the surface of an ELISA plate. Excess of unlabelled reference antibody may be added for about 15 minutes and subsequently biotinylated test antibodies may be added. After washes in PBS/Tween, binding of the test biotinylated antibody may be detected using horseradish peroxidase (HRP)-conjugated streptavidin and the signal detected using standard methods. It is readily apparent that in the competition assays, the reference antibody may be labeled and the test antibody unlabeled. The test antibody competes with the reference antibody when the reference antibody inhibits binding of the test antibody, or the test antibody inhibits binding of the reference antibody by at least 80%, 85%, 90% , 95% or 100%. The epitope of the test antibody may further be defined for example by peptide mapping or hydrogen/deuterium protection assays using known methods, or by crystal structure determination.

An anti-CD38 antibody binds to the region SKRNIQFSCKNIYR (SEQ ID NO: 2) and the region EKVQTLEAWVIHGG (SEQ ID NO: 3) of human CD38 (SEQ ID NO: 1) when the antibody binds at least 1, 2, 3, 4, 5, 6, 7, 8, 9, 10, 11, 12, 13 or 14 residues within SEQ ID NO: 2 and SEQ ID NO: 3. In some embodiments, the anti-CD38 antibody binds at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments, the anti-CD38 antibody binds at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments, the anti-CD38 antibody binds at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1).

An exemplary antibody that binds to the region SKRNIQFSCKNIYR (SEQ ID NO: 2) and the region EKVQTLEAWVIHGG (SEQ ID NO: 3) of human CD38 (SEQ ID NO: 1) is DARZALEX™ (daratumumab).

Antibodies binding to the region SKRNIQFSCKNIYR (SEQ ID NO: 2) and the region EKVQTLEAWVIHGG (SEQ ID NO: 3) of human CD38 (SEQ ID NO: 1) may be generated for example by immunizing mice with peptides having the amino acid sequences shown in SEQ ID NOs: 2 and 3 using standard methods and as described herein, and characterizing the obtained antibodies for binding to the peptides using for example ELISA or mutagenesis studies.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC), as described in more detail below. Such functions may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, e.g., CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

In some embodiments, the anti-CD38 antibody is of IgG1, IgG2, IgG3 or IgG4 isotype.

In some embodiments, the anti-CD38 antibody is of IgG1 isotype.

In some embodiments, the anti-CD38 antibody is of IgG2 isotype.

In some embodiments, the anti-CD38 antibody is of IgG3 isotype.

In some embodiments, the anti-CD38 antibody is of IgG4 isotype.

In some embodiments, the anti-CD38 antibody induces killing of CD38-expressing cells by antibody-dependent cellular cytotoxicity (ADCC), antibody-dependent cellular phagocytosis (ADCP), complement-dependent cytotoxicity (CDC) or apoptosis.

In some embodiments, the anti-CD38 antibody induces killing of CD38-expressing cells by ADCC.

In some embodiments, the anti-CD38 antibody induces killing of CD38-expressing cells by ADCP.

In some embodiments the anti-CD38 antibody induces killing of CD38-expressing cells by CDC.

In some embodiments, the anti-CD38 antibody induces killing of CD38-expressing cells by apoptosis.

"Antibody-dependent cellular cytotoxicity," "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcγRIIIa. Death of the antibody-coated target cell, such as CD38-expressing MM cell, occurs as a result of effector cell activity through the secretion of membrane pore-forming proteins and proteases. To assess ADCC activity of an anti-CD38 antibody, the antibody may be added to CD38-expressing cells in combination with immune effector cells, which may be activated by the antigen antibody complexes resulting in cytolysis of the target cell. Cytolysis may be detected by the release of label (e.g., radioactive substrates, fluorescent dyes or natural intracellular proteins) from the lysed cells. Exemplary effector cells for such assays include peripheral blood mononuclear cells (PBMC) and NK cells. Multiple myeloma cell lines or primary MM cells that express CD38 may be used as target cells. In an exemplary assay, MM cell lines engineered to express luciferase are incubated with anti-CD38 antibodies. Freshly isolated PBMC effector cells are added at target:effector cell ratio of 40:1. 4 hours after addition of PBMC, luciferin is added and the resulting bioluminescent signal emitted from surviving MM cells determined within 20 minutes using a luminometer (SpectraMax, Molecular Devices), and the percentage ADCC of MM cells can calculated using the formula: % ADCC=1−(mean bioluminescent signal in the absence of PBMCs/mean bioluminescent signal in the presence of PBMCs)×100%. Anti-CD38 antibody "induces ADCC in vitro" when % ADCC in an in vitro assay such as one described above is at least about 20%, 25%, 30%, 35%, 40%, 45%, 50%, 55%, 60%, 65%, 70%, 80%, 90% or 100%

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. In an exemplary assay, primary BM-MNC cells isolated from a patient with a B-cell malignancy may be treated with an anti-CD38 antibody and complement derived from 10% pooled human serum for 1 hour at a concentration of 0.3-10 μg/ml, and the survival of primary CD138+ MM cells may be determined by flow cytometry using techniques described in van der Veer et al., Haematologica 96:284-290, 2011; van der Veer et al., Blood Cancer J 1(10):e41, 2011. The percentage of MM cell lysis may be determined relative to an isotype control as described herein. Anti-CD38 antibodies used in the methods of the invention may induce CDC by about 20%, 25%, 30%, 35%, 40%, 45%, 50%, 55%, 60%, 65%, 70%, 75%, 80%, 85%, 90%, 95% or 100%

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma tumor cells expressing CD38 as target cells engineered to express GFP or other labeled molecule. Effector:target cell ratio may be, for example, 4:1. Effector cells may be incubated with target cells for 4 hours with or without anti-CD38 antibody. After incubation, cells may be detached using accutase. Macrophages may be identified with anti-CD11b and anti-CD14 antibodies coupled to a fluorescent label, and percent phagocytosis may be determined based on % GFP fluorescent in the CD11$^+$CD14$^+$ macrophages using standard methods. Anti-CD38 antibodies used in the methods of the invention may induce ADCP by about 20%, 25%, 30%, 35%, 40%, 45%, 50%, 55%, 60%, 65%, 70%, 75%, 80%, 85%, 90%, 95% or 100%.

ADCC elicited by anti-CD38 antibodies may be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

In some embodiments, the anti-CD38 antibodies comprise an amino acid substitution in the antibody Fc.

In some embodiments, the anti-CD38 antibodies comprise a substitution in the antibody Fc at amino acid positions 256, 290, 298, 312, 356, 330, 333, 334, 360, 378 or 430 (residue numbering according to the EU index).

ADCC elicted by anti-CD38 antibodies can also be enhanced by engineering the antibody oligosaccharide component. Human IgG1 or IgG3 are N-glycosylated at Asn297 with the majority of the glycans in the biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such modified antibodies can be achieved using different methods reported to lead to the successful expression of relatively high defucosylated antibodies bearing the biantennary complex-type of Fc oligosaccharides such as control of culture osmolality (Konno et al., Cyto-technology 64(:249-65, 2012), application of a variant CHO line Lec13 as the host cell line (Shields et al., J Biol Chem 277:26733-26740, 2002), application of a variant CHO line EB66 as the host cell line (Olivier et al., MAbs ;2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng88:901-908, 2004), or coexpression of β1-1,4-N-acetyl-glucosaminyltransferase III and Golgi α-mannosidase II or a potent alpha-mannosidase I inhibitor, kifunensine (Ferrara et al., J Biol Chem281:5032-5036, 2006, Ferrara et al., Biotechnol Bioeng 93:851-861, 2006; Xhou et al., Biotechnol Bioeng 99:652-65, 2008).

In some embodiments, the anti-CD38 antibody has a biantennary glycan structure with fucose content between about 0% to about 15%, for example 15%, 14%, 13%, 12%, 11% 10%, 9%, 8%, 7%, 6%, 5%, 4%, 3%, 2%, 1% or 0%.

In some embodiments, the anti-CD38 antibody has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the anti-CD38 antibody.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546 2); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the antibody to constituent peptides by enzymatic digestion (e.g., trypsin or endopeptidase Lys-C), and subsequent separation, detection and quantitation by HPLC-MS (UPLC-MS); 5) Separation of the antibody oligosaccharides from the antibody protein by specific enzymatic deglycosylation with PNGase F at Asn 297. The oligosaccharides thus released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0% to about15%.

"Normal fucose" or 'normal fucose content" as used herein refers to antibodies with fucose content of about over 50%, typically about over 80% or over 85%.

Antibodies that are substantially identical to the antibody comprising the heavy chain of SEQ ID NO: 12 and the light chain of SEQ ID NO: 13 may be used in the methods of the invention. The term "substantially identical" as used herein means that the two antibody heavy chain or light chain amino acid sequences being compared are identical or have "insubstantial differences". Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings. Exemplary substitutions that can be made to the anti-CD38 antibodies used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made, for example, to the heavy or the light chain of the anti-CD38 antibody. Furthermore, any native residue in the heavy or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired Amino acid substitutions may be done for example by PCR mutagenesis (U.S. Pat. No. 4,683,195). Libraries of variants may be generated using well-known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38 and their ability to induce ADCC using methods described herein.

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand Suppl* 643:55-67; Sasaki et al., (1988) *Adv Biophys* 35:1-24). Amino acid substitutions to the antibodies of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

In some embodiments, the anti-CD38 antibody may bind human CD38 with a range of affinities ($K_D$). In one embodiment, the anti-CD38 antibody binds to CD38 with a $K_D$ equal to or less than about $1\times10^{-8}$ M, for example $5\times10^{-9}$M, $1\times10^{-9}$ M, $5\times10^{-10}$ M, $1\times10^{-10}$ M, $5\times10^{-11}$M, $1\times10^{-11}$ M, $5\times10^{-12}$M, $1\times10^{-12}$ M, $5\times10^{-13}$M, $1\times10^{-13}$ M, $5\times10^{-14}$M, $1\times10^{-14}$ M or $5\times10^{-15}$ M, or any range or value therein, as determined by surface plasmon resonance or the Kinexa method, as practiced by those of skill in the art. An exemplary affinity is equal to or less than $1\times10^{-8}$ M. Another exemplary affinity is equal to or less than $1\times10^{-9}$ M.

KinExA instrumentation, ELISA or competitive binding assays known to those skilled in the art. The measured affinity of a particular antibody/CD38 interaction may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. Therefore the term "about" in the context of $K_D$ reflects the typical standard deviation in the assay. For example, the typical SD for a $K_D$ of $1\times10^{-9}$ M is up to $\pm0.33\times10^{-9}$M.

In some embodiments, the anti-CD38 antibody is a bispecific antibody. The VL and/or the VH regions of existing anti-CD38 antibodies or the VL and VH regions identified de novo as described herein may be engineered into bispecific full length antibodies. Such bispecific antibodies may be made by modulating the CH3 interactions in antibody Fc to form bispecific antibodies using technologies such as those described in U.S. Pat. No. 7,695,936; Int. Pat. Publ. No. WO04/111233; U.S. Pat. Publ. No. U52010/0015133; U.S. Pat. Publ. No. US2007/0287170; Int. Pat. Publ. No. WO2008/119353; U.S. Pat. Publ. No. US2009/0182127; U.S. Pat. Publ. No. US52010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876.

For example, bispecific antibodies of the invention may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody (e.g., anti-CD38 antibody) and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl) phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

Additional bispecific structures into which the VL and/or the VH regions of the antibodies of the invention may be incorporated are for example Dual Variable Domain Immunoglobulins (DVD) (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441). DVDs are full length antibodies comprising the heavy chain having a structure VH1-linker-VH2-CH and the light chain having the structure VL1-linker-VL2-CL; linker being optional.

In some embodiments, the anti-CD38 antibody is conjugated to a toxin. Conjugation methods and suitable toxins are well known.

In some embodiments, the subject having MM is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor IIIa (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158FN polymorphisms demonstrates reduced Fc engagement and therefore reduced ADCC when compared to the FcγRIIIa-158V/

V. The lack of or low amount of fucose on human N-linked oligosaccharides improves the ability of the antibodies to induce ADCC due to improved binding of the antibodies to human FcγRIIIa (CD16) (Shields et al., J Biol Chem 277: 26733-40, 2002). Patients can be analyzed for their FcγRIIIa polymorphism using routine methods.

In some embodiments, the survivin inhibitor is a small molecule.

In some embodiments, the survivin inhibitor is a polynucleotide.

Survivin inhibitors may inhibit survivin-induced apoptosis by any mechanism, such as inhibiting survivin gene transcription or protein expression, inhibiting survivin protein dimerization, enhancing destabilization or inducing its degradation, etc.

An exemplary survivin small molecule inhibitor is YM155. YM155 binds to the survivin promoter and inhibits its transcription. Other exemplary survivin small molecule inhibitors are, for example, nordihydroguaiaretic acid derivatives as described in U.S. Pat. No. 6,608,108, and molecules described in U.S. Pat. Publ. No. US2012/0122910. Other survivin polynucleotide inhibitors are described, for example, in U.S. Pat. No. 6,838,283, Intl. Pat. Publ Nos. WO01/057059, WO09/114476 and WO09/044793. Polynucleotide inhibitors include microRNAs (miRNAs), small intereference RNAs (siRNAs), allele specific oligos (ASOs) and other polynucleotide inhibitors know in the art.

Administration/Pharmaceutical Compositions

In the methods of the invention, the anti-CD38 antibodies may be provided in suitable pharmaceutical compositions comprising the anti-CD38 antibody and a pharmaceutically acceptable carrier. The carrier may be diluent, adjuvant, excipient, or vehicle with which the anti-CD38 antibody is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration of the anti-CD38 antibody in the methods of the invention may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-CD38 antibody in the methods of the invention may be may administered to a patient by any suitable route, for example parentally by intravenous (IV) infusion or bolus injection, intramuscularly or subcutaneously or intraperitoneally. IV infusion can be given over for example 15, 30, 60, 90, 120, 180, or 240 minutes, or from 1, 2, 3, 4, 5, 6, 7, 8, 9, 10, 11 or 12 hours.

The dose given to a patient having CD38-positive hematological malignancy is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat MM, but 9, 10, 11, 12, 13, 14, 15, 16, 17, 18, 19, 20 or more doses may be given.

The administration of the anti-CD38 antibody in the methods of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-CD38 antibody in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/ kg or at 16 mg/kg every four weeks by intravenous infusion.

The anti-CD38 antibodies may be administered in the methods of the invention by maintenance therapy, such as, e.g., once a week for a period of 6 months or more.

For example, anti-CD38 antibodies in the methods of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Anti-CD38 antibodies in the methods of the invention may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-CD38 antibody in the methods of the invention may be lyophilized for storage and reconstituted in a suitable carrier prior to use. This technique has been shown to be effective with conventional protein preparations and well known lyophilization and reconstitution techniques can be employed.

In the methods of the invention, the anti-CD38 antibody is administered in combination with a survivin inhibitor.

In the methods of the invention, the anti-CD38 antibody is administered in combination with a survivin inhibitor YM155.

YM155 used in the methods of the invention is readily available according to the processes of production as disclosed in International Publication Intl. Pat. Publ. Nos. WO01/60803 and WO2004/092160.

YM155 may be administered orally or parenterally, or intravenously. In this connection, the injection preparation for intravenous administration includes those containing sterile aqueous or non-aqueous solutions, suspensions, and emulsions. The aqueous solvent includes, for example, distilled water for injection and physiological saline. The non-aqueous solvent includes, for example, propylene glycol, polyethylene glycol, vegetable oils such as olive oil, alcohols such as ethanol, polysorbate 80, and the like. Such compositions may contain further tonicity adjusting agents, antiseptics, moistening agents, emulsifying agents, dispersing agents, stabilizers, and solubilizing agents. These may be sterilized, for example, by filtration through a bacterial filter, blending of sterilizers or irradiation. Alternatively, it is possible to prepare a germ-free solid composition and dissolve or suspend it in sterile water or a sterile solvent for injection immediately before use.

In intravenous administration, YM155 may be administered, for example, at 0.1-20 mg/m$^2$/day, such as at 1-10 mg/m$^2$/day, once a day or divided in plural doses, or continuously by infusion (continuous instillation). YM155 may be infused at 3-10 mg/m$^2$/day continuously for a period of 4 days to 20 days, for example 4 days to 14 days, or 5 days, 7 days, 10 days or 14 days, and or for 7 days. When the administration is further continued, a medication cycle may be employed comprising a term of drug holidays of 1 day to 2 months, 7 days to 21 days, or 14 days, after termination of the above term of medication. Alternatively, YM155 may be administered continuously by infusion at a dose of 3-8 mg/m$^2$/day for 7 days, followed by drug holidays of 14 days; this cycle as one cycle is repeated depending on the conditions. The frequency of administration, dosage, time of infusion, medication cycle, and the like, may be determined properly according to individual cases considering the kind of anticancer agent, state of the patients, age, gender, etc.

In the methods of the invention, the combination of the anti-CD38 antibody and survivin inhibitor may be administered over any convenient timeframe. For example, the anti-CD38 antibody and survivin inhibitor may be administered to a patient on the same day. However, the anti-CD38 antibody and survivin may also be administered on alternating days or alternating weeks or months, and so on. In some methods, the anti-CD38 antibody and survivin inhibitor may be administered with sufficient proximity in time that they are simultaneously present (e.g., in the serum) at detectable levels in the patient being treated. In some methods, an entire course of treatment with the anti-CD38 antibody consisting of a number of doses over a time period is followed or preceded by a course of treatment with survivin inhibitor, consisting of a number of doses. A recovery period of 1, 2 or several days or weeks may be used between administration of the anti-CD38 antibody and survivin inhibitor.

Anti-CD38 antibody in combination with survivin inhibitor may be administered together with any form of radiation therapy including external beam radiation, intensity modulated radiation therapy (IMRT) and any form of radiosurgery including Gamma Knife, Cyberknife, Linac, and interstitial radiation (e.g., implanted radioactive seeds, GliaSite balloon), and/or with surgery.

Subcutaneous administration of pharmaceutical compositions comprising an antibody that specifically binds CD38 and a hyaluronidase The anti-CD38 antibody may be administered as a pharmaceutical composition comprising the anti-CD38 antibody and a hyaluronidase subcutaneously.

The concentration of the anti-CD38 antibody in the pharmaceutical composition administered subcutaneously may be about 20 mg/ml.

The pharmaceutical composition administered subcutaneously may comprise between about 1,200 mg-1,800 mg of the anti-CD38 antibody.

The pharmaceutical composition administered subcutaneously may comprise about 1,200 mg of the anti-CD38 antibody.

The pharmaceutical composition administered subcutaneously may comprise about 1,600 mg of the anti-CD38 antibody.

The pharmaceutical composition administered subcutaneously may comprise about 1,800 mg of the anti-CD38 antibody.

The pharmaceutical composition administered subcutaneously may comprise between about 30,000U-45,000 U of the hyaluronidase.

The pharmaceutical composition administered subcutaneously may comprise about 1,200 mg of the anti-CD38 antibody and about 30,000 U of the hyaluronidase.

The pharmaceutical composition administered subcutaneously may comprise about 1,800 mg of the anti-CD38 antibody and about 45,000 U of the hyaluronidase.

The pharmaceutical composition administered subcutaneously may comprise about 1,600 mg of the anti-CD38 antibody and about 30,000 U of the hyaluronidase.

The pharmaceutical composition administered subcutaneously may comprise about 1,600 mg of the anti-CD38 antibody and about 45,000 U of the hyaluronidase.

The pharmaceutical composition administered subcutaneously may comprise the hyaluronidase rHuPH20 having the amino acid sequence of SEQ ID NO: 23.

rHuPH20 is a recombinant hyaluronidase (HYLENEX® recombinant) and is described in Int. Pat. Publ. No. WO2004/078140.

Hyaluronidase is an enzyme that degrades hyaluronic acid (EC 3.2.1.35) and lowers the viscosity of hyaluronan in the extracellular matrix, thereby increasing tissue permeability.

SEQ ID NO: 23
MGVLKFKHIFFRSFVKSSGVSQIVFTFLLIPCCLTLNFRAPPVIPNVP

FLWAWNAPSEFCLGKFDEPLDMSLFSFIGSPRINATGQGVTIFYVDRL

GYYPYIDSITGVTVNGGIPQKISLQDHLDKAKKDITFYMPVDNLGMAV

IDWEEWRPTWARNWKPKDVYKNRSIELVQQQNVQLSLTEATEKAKQEF

EKAGKDFLVETIKLGKLLRPNHLWGYYLFPDCYNHHYKKPGYNGSCFN

VEIKRNDDLSWLWNESTALYPSIYLNTQQSPVAATLYVRNRVREAIRV

SKIPDAKSPLPVFAYTRIVFTDQVLKFLSQDELVYTFGETVALGASGI

VIWGTLSIMRSMKSCLLLDNYMETILNPYIINVTLAAKMCSQVLCQEQ

GVCIRKNWNSSDYLHLNPDNFAIQLEKGGKFTVRGKPTLEDLEQFSEK

FYCSCYSTLSCKEKADVKDTDAVDVCIADGVCIDAFLKPPMETEEPQI

FYNASPSTLSATMFIVSILFLIISSVASL

The administration of the pharmaceutical composition comprising the anti-CD38 antibody and the hyaluronidase may be repeated after one day, two days, three days, four days, five days, six days, one week, two weeks, three weeks, four weeks, five weeks, six weeks, seven weeks, two months, three months, four months, five months, six months or longer. Repeated courses of treatment are also possible, as is chronic administration. The repeated administration may be at the same dose or at a different dose. For example, the pharmaceutical composition comprising the anti-CD38 antibody and the hyaluronidase may be administered once weekly for eight weeks, followed by once in two weeks for 16 weeks, followed by once in four weeks. The pharmaceutical compositions to be administered may comprise about 1,200 mg of the anti-CD38 antibody and about 30,000 U of hyaluronidase, wherein the concentration of the antibody that specifically binds CD38 in the pharmaceutical composition is about 20 mg/ml. The pharmaceutical compositions to be administered may comprise about 1,800 mg of the anti-CD38 antibody and about 45,000 U of hyaluronidase. The pharmaceutical compositions to be administered may comprise about 1,600 mg of the anti-CD38 antibody and about 30,000 U of hyaluronidase. The pharmaceutical compositions to be administered may comprise about 1,600 mg of the anti-CD38 antibody and about 45,000 U of hyaluronidase.

The pharmaceutical composition comprising the anti-CD38 antibody and the hyaluronidase may be administered subcutaneously to the abdominal region.

The pharmaceutical composition comprising the anti-CD38 antibody and the hyaluronidase may be administered in a total volume of about 80 ml, 90 ml, 100 ml, 110 ml or 120 ml.

For administration, 20 mg/ml of the anti-CD38 antibody in 25 mM sodium acetate, 60 mM sodium chloride, 140 mM D-mannitol, 0.04% polysorbate 20, pH 5.5 may be mixed with rHuPH2O, 1.0 mg/mL (75-150 kU/mL) in 10 mM L-Histidine, 130 mM NaCl, 10 mM L-Methionine, 0.02% Polysorbate 80, pH 6.5 prior to administration of the mixture to a subject.

While having described the invention in general terms, the embodiments of the invention will be further disclosed in the following examples that should not be construed as limiting the scope of the claims.

Materials and Methods

Cells and Cell culture

Bone marrow mononuclear cells (BM-MNCs) and peripheral blood mononuclear cells (PBMCs)

BM aspirates from MM patients or healthy individuals, as well as PB from healthy individuals were collected using protocols and procedures approved by the institutional medical ethical committee in accordance with the declaration of Helsinki. Healthy Donor (HD)-PBMCs and BM-MNCs were isolated by Ficoll-Hypaque density-gradient centrifugation from PB samples or BM aspirates respectively. PBMCs were used directly as effector cells in ADCC experiments; BM-MNCs were cryopreserved until use.

Multiple Myeloma (MM) cell lines

The luciferase (Luc)-transduced human MM cell lines RPMI-8226 and UM9 were maintained in RPMI1640 (Invitrogen), supplemented with 10% fetal bovine serum (FBS; Integro BV) and antibiotics (penicillin/streptomycin; Life Technologies) at 37° C. in a humidified atmosphere containing 5% $CO_2$.

Bone marrow stromal cells (BMSC)

Adherent stromal cells were isolated and cultured from BM-MNCs of healthy individuals (hBMSC) or of MM patients (pBMSC) by plastic adherence. Cells were cultured in Optimem (Invitrogen) with 5% platelet lysate, heparin and antibiotics. hBMSCs were used in experiments until passage six and pBMSC were used after passage one or two.

Reagents

YM155 (Sepantronium Bromide; 4,9-Dihydro-1-(2-methoxyethyl)-2-methyl-4,9-dioxo-3-(2-pyrazinylmethyl)-1H-naphth[2,3-d]imidazolium bromide; CAS 781661-94-7) (Selleck Chemicals) was dissolved in dimethylsulfoxide (DMSO) at a concentration of 1mM and aliquoted for storage until use. YM155 was diluted in culture medium to the concentrations indicated in each experiment.

YM155; Formula I:

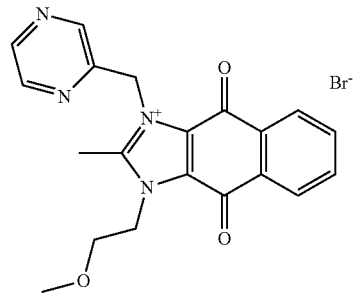

Compartment specific bioluminescence based Antibody dependent cell-mediated cytotoxicity (ADCC) against Multiple Myeloma cell lines ("compartment-specific BLI-based cytotoxicity assays")

hBMSC were plated at a density of $1\times10^4$ cells/well in white opaque flat-bottomed 96-well plates (Costar) in 100 µl culture medium. After an adherence period of six hours, luc-transduced MM cell lines were added at a density of $1\times10^4$ cells/well in BMSC-coated or uncoated wells. In experiments in which YM155 was tested, YM155 was added at indicated concentrations together with MM cells. After 16-20 hours, daratumumab was added at indicated concentrations and left for 15 minutes at room temperature. Freshly isolated PBMC from healthy individuals were then added as effector cells at the indicated effector target ratios. 4 hours after addition of PBMC, 125 µg/ml beetle luciferin (Promega) was added and the bioluminescent signal emitted from surviving MM cells was determined within 20 minutes using a luminometer (SpectraMax, Molecular Devices). The percentage survival of MM cells was calculated using the formula: % survival=(mean bioluminescent signal in the absence of PBMCs/mean bioluminescent signal in the presence of PBMCs)×100%. In these assays the survival of MM cells is a direct reflection of ADCC mediated lysis and correlates with classical chromium release assays as described in McMillin et al., Nat Med 16:483-489, 2010.

FACS based ADCC assay in Multiple Myeloma BM-MNC

Frozen BM-MNCs from MM patients with 15-35% $CD138^+$ MM cells were used in FACS-based ADCC assays. The cells were thawed and cultured in 10% HS in RPMI. After 16-20 h, BM-MNCs were counted by trypan blue exclusion and $4\times10^4$ cells/well were plated in 96 round bottom plates. Daratumumab and/or YM155 were added in the wells as indicated per experiment. After 24 hours, cells were stained with fluorescent conjugated anti-CD138, anti-CD38, anti-CD56 and anti-CD3 antibodies and the survival of primary CD138+ MM cells in the BM-MNCs was determined by FACS as previously described (Groen et al., Blood 120:e9-e16, 2012). Percentage lysis of MM cells was deduced using the following formula: % lysis cells=1−(counts of surviving CD138+ cells in treated wells/counts of number of surviving CD138+ cells in control wells)×100%.
Flow cytometry To determine the level of CD38 expression on MM cells, MM cells were cultured alone or with BMSCs and incubated with CD38 fluorescein conjugated antibody. The cells were additionally stained with CD105 as a marker for BMSCs. The CD38 expression on CD105 negative cells was determined by FACS as described (de Haart et al., Clin Cancer Res 19:5591-601, 2013).
In vivo tumor targeting experiments Hybrid scaffolds consisting of three 2- to 3-mm biphasic calcium phosphate particles coated with HD-BMSC were in vitro loaded with Luc+ MM cell line UM9 ($1\times10^6$ cells/scaffold) before s.c. implantation into RAG2$^{31}$ $^{-/-}$γc$^{-/-}$ mice as described previously (Groen et al., Blood 120:e9-e16, 2012). Ten days after implantation, mice with tumors growing in the scaffolds were treated with vehicle control, daratumumab+PBS or daratumumab+YM155. Each mice, including the control group, received in addition T cell-depleted HD-PBMCs ($5\times10^6$ cells) as a source of human NK cells to induce ADCC. PBS and YM155-diluted in PBS were administered using ssubcutaneous infusion pumps (Alzet 1007D) delivering 1 mg/kg/d of the drug continuously. Pumps were removed after 10 days. BLI was performed as described previously (Spaapen et al., Clin Cancer Res 16:5481-88, 2010; Rozemuller et al., Haematologica 93:1049-57, 2008).
Granzyme B Enzyme linked immunosorbent assay (ELISA)

The granzyme B (GzB) content of cell-free supernatants was determined using a commercial ELISA kit (Pelipair, Sanquin, Amsterdam, NL) according to the manufacturer's instructions.

EXAMPLE 1

Bone Marrow stromal cells confer protection against antibody-dependent cellular cytotoxicity of multiple myeloma cells Since the stromal cells of bone marrow (BM) microenvironment protect MM cells against CTL and NK mediated cytotoxicity, it was evaluated whether a similar protective effect occurs against antibody-dependent cellular cytotoxicity (ADCC) induced by daratumumab.

Figure 1B:
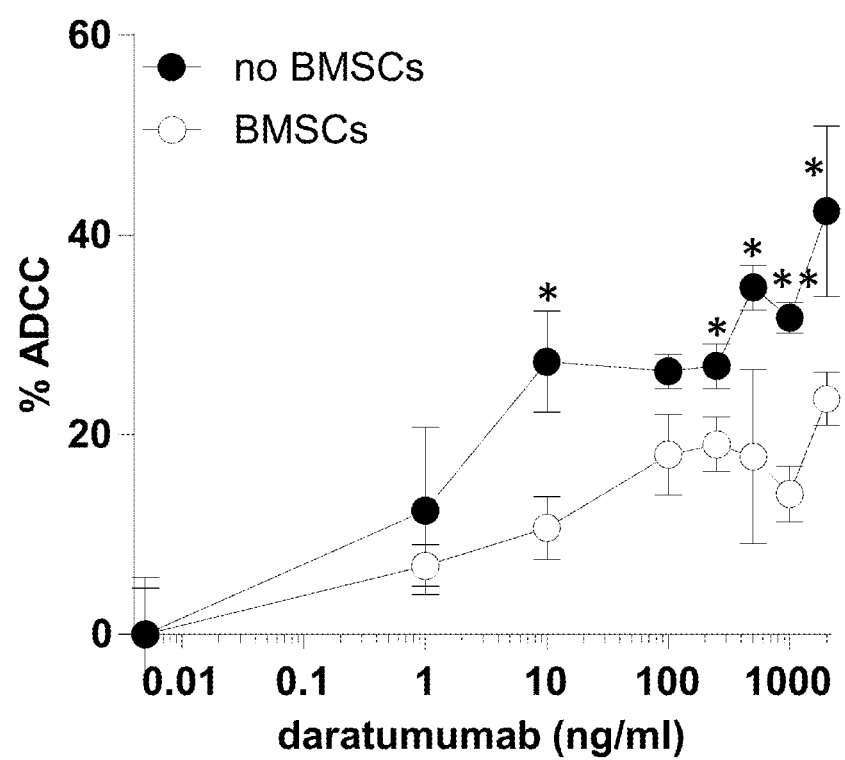
FIG. 1B. Bone Marrow stromal cells (BMSCs) mediate protection against multiple myeloma (MM) cell killing by ADCC induced by anti-CD38 antibody daratumumab in MM cell lines. Luciferase transduced $CD38^+$ RPMI8226 MM cells were cultured in the presence or absence of HD-BMSCs for 16 hours prior to incubation with serial concentrations of daratumumab and HD-PBMCs at a PBMC:MM cell ratio of 30:1. MM cell viability was determined after 4 hours by BLI. % ADCC was calculated relative to the cell viability without daratumumab. Error bars indicate the SEM of triplicate measurements. The data are representative for 3 independent experiments. The differences between cultures with or without BMSCs were tested with an unpaired t test *=$p<0.05$.

Induction of ADCC by healthy donor BMSCs against two CD38+ luciferase transduced MM cell lines, UM9 and RPMI was tested with serial concentrations of daratumumab in the presence or absence of HD-PBMCs as effector cells in compartment-specific BLI-based cytotoxicity assays. In the absence of BMSCs, daratumumab mediated ADCC in both MM cell lines in a dose dependent fashion. Both cell lines were less sensitive to daratumumab-induced ADCC in the presence of BMSCs. FIG. 1A shows the effect of BMSCs on daratumumab-induced ADCC in UM9 cells, and FIG. 1B shows the effect of BMSCs on daratumumab-induced ADCC in RPMI-8226 cells.

Figure 2A:
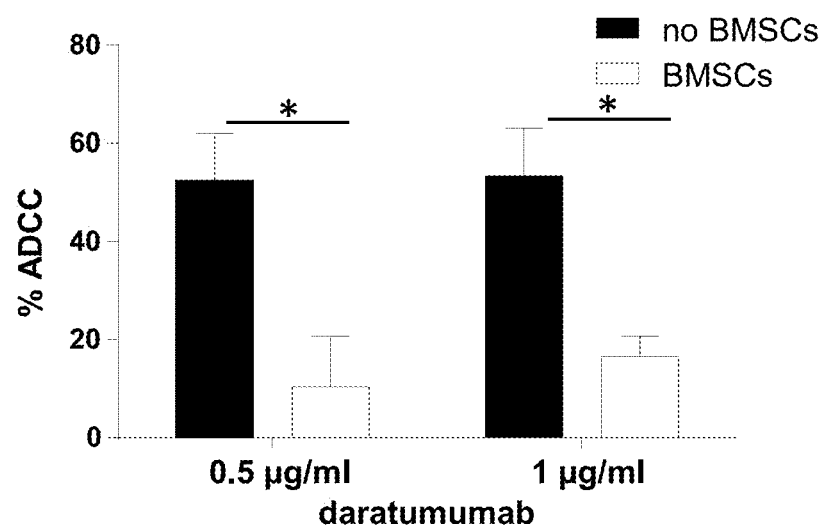
FIG. 2A. BMSCs mediate protection against MM cell killing by ADCC induced by anti-CD38 antibody daratumumab in primary MM patient samples. Full Bone marrow aspirates obtained from MM patient 1 was cultured in the presence (white bars) or absence (black bars) of autologous bone marrow stromal cells and then treated with daratumumab at indicated concentrations. The autologous cells present in aspirate were used as effector cells. Since BM-MNCs already contain NK cells as effector cells, no additional effector cells were added. The viability of $CD138^+$ MM cells in the cultures was determined after 24 hours by flow cytometry. Error bars indicate the SEM of triplicate measurements. The differences between cultures with or without BMSCs were tested with an unpaired t test. *=$p<0.05$. Top panel: patient #1, Bottom panel; patient #2. BMSC: bone marrow stromal cell. ADCC: antibody-dependent cell cytotoxicity.
Figure 2B:
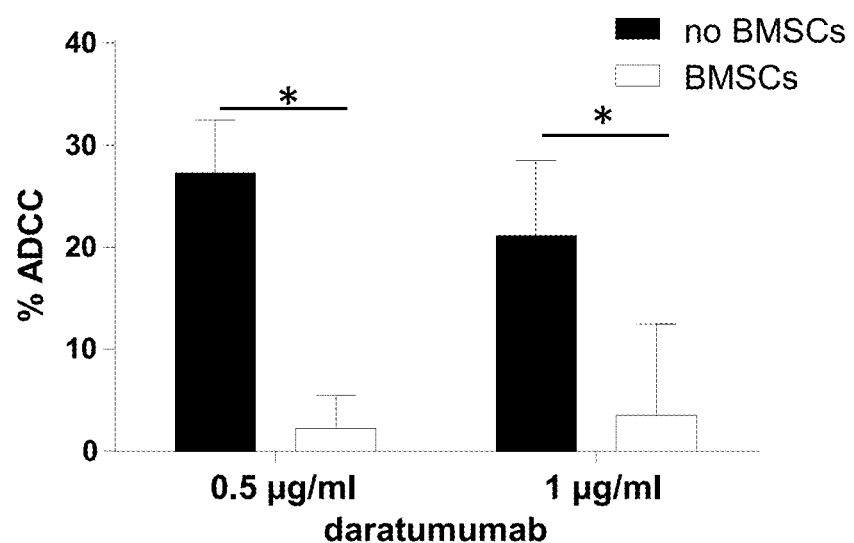
FIG. 2B. BMSCs mediate protection against MM cell killing by ADCC induced by anti-CD38 antibody daratumumab in primary MM patient samples. Full Bone marrow aspirates obtained from MM patient 2 was cultured in the presence (white bars) or absence (black bars) of autologous bone marrow stromal cells and then treated with daratumumab at indicated concentrations. The autologous cells present in aspirate were used as effector cells. Since BM-MNCs already contain NK cells as effector cells, no additional effector cells were added. The viability of CD138+ MM cells in the cultures was determined after 24 hours by flow cytometry. Error bars indicate the SEM of triplicate measurements. The differences between cultures with or without BMSCs were tested with an unpaired t test. *=p=0.05. Top panel: patient #1, Bottom panel; patient #2. BMSC: bone marrow stromal cell. ADCC: antibody-dependent cell cytotoxicity.

Ability of BMSCs to protect primary MM cells from daratumumab-induced ADCC was also evaluated in a FACS-based ADCC assay using methodology described above. In the assays, BM-MNCs containing at least 15% CD138+ malignant plasma cells and sufficient numbers of autologous effector NK cells were incubated with daratumumab to induce ADCC. The BM-MNCs were tested either alone or in co-culture with autologous BMSCs to evaluate the effect of BMSCs. FACS-based viability assay was performed after 24 hours of culture to determine CD138+ surviving cells and calculate lysis. Induction of ADCC of primary MM cells was less efficient in the presence of autologous MM-BMSCs in both donors tested (FIG. 2A and FIG. 2B), indicating that the stromal cells of the tumor microenvironment induced a resistance to daratumumab therapy.

EXAMPLE 2

BMSC-induced suppression of ADCC is not caused by CD38 down-regulation or NK cell suppression Possible changes in CD38 surface expression and NK cell activation were evaluated to understand the mechanisms of BMSC-mediated protection against ADCC.

MM cell lines UM9 and RPMI-8226 were cultured in the presence or absence of healthy donor BMSCs. Co-culture of MM cells with BMSCs did not down-regulate the CD38 expression levels on either MM cell line (data not shown).

Since BMSCs are known to produce several immunosuppressive factors such as IDO, TGF-β or PGE-2, the protection against ADCC by BMSCs could be due to the suppression of NK-cell activation, which would reduce their ability to degranulate and release granzyme B and perforin in the immune synapses to kill their targets. To that end, effect of BMSCs on NK cell activation by daratumumab was determined using daratumumab-mediated granzyme B excretion as a marker for NK cell activity. Granzyme B levels were in general higher in the supernatants in the presence pf BMSCs (data not shown). Hence, BMSC-mediated protection against ADCC was likely not due to NK cell suppression.

EXAMPLE 3

Survivin inhibition abrogates BMSC-mediated protection against ADCC and provides synergistic ADCC-mediated killing of multiple myeloma cells with daratumumab BMSCs have been shown to protect MM cells against CTL lysis by up-regulation of survivin in MM cells. Modulation of survivin was evaluated as a possible mechanism for BMSC-mediated protection against ADCC induced by daratumumab using YM155, a small molecule inhibitor of survivin.

Figure 3:
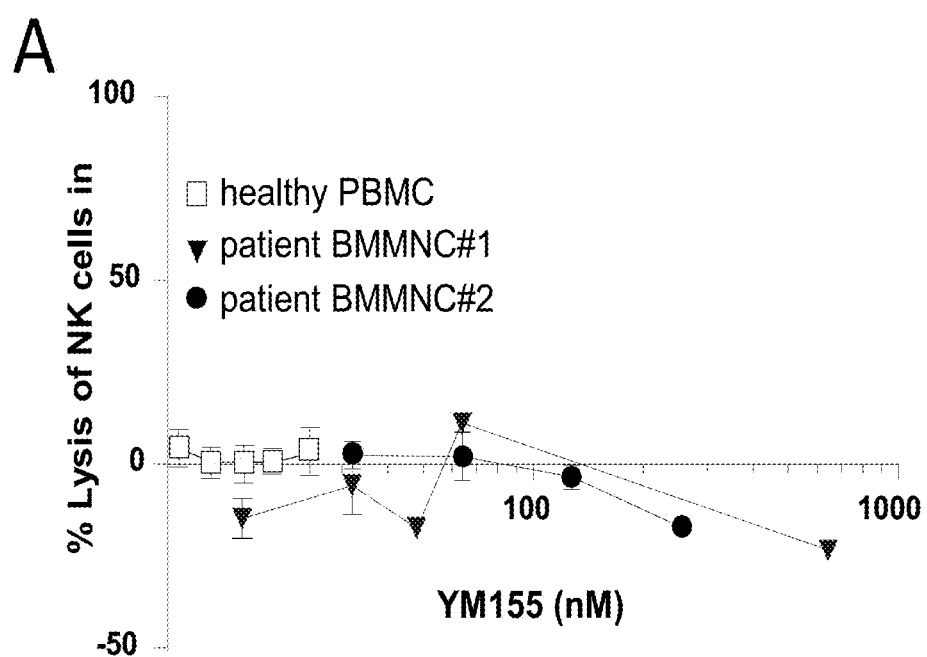
FIG. 3. YM155 does not induce NK cell lysis. HD-PBMCs and patient bone marrow mononuclear cells (BM-MNCs) were incubated with the indicated concentrations of YM155 for 24 hours. The number of viable $CD3^-CD56^+$ NK cells was determined by flow cytometry and the percent lysis was calculated using the untreated samples as negative control.

Effect of YM155 on NK cell viability was evaluated first. BM-MNCs of MM patients were cultured in the presence of different doses of YM155 for 24 hours. Viability of MM cells (CD138+ cells) and NK cells (CD3−CD138−CD56+ cells) were determined by FACS. NK cells were not affected at YM155 doses which already showed some toxicity to MM cells (FIG. 3).

Effect of daratumumab, YM155, or a combination of daratumumab and YM155 was evaluated in RPMI-8226 cells and in two MM patient samples using YM155 concentrations shown to be non-toxic to NK cells.

In the assays, daratumumab and YM155 were used at a concentration of 0.3 μg/ml and 1 nM, respectively, for RPMI-8226 cells and at a concentration of 1 μg/ml and 120 nM for MM patient samples, respectively. Healthy donor PBMCs were used as effector cells at effector:target cell ratio of 40:1 for RPMI-8226 cells and 30:1 for MM patient samples.

Figure 4A:
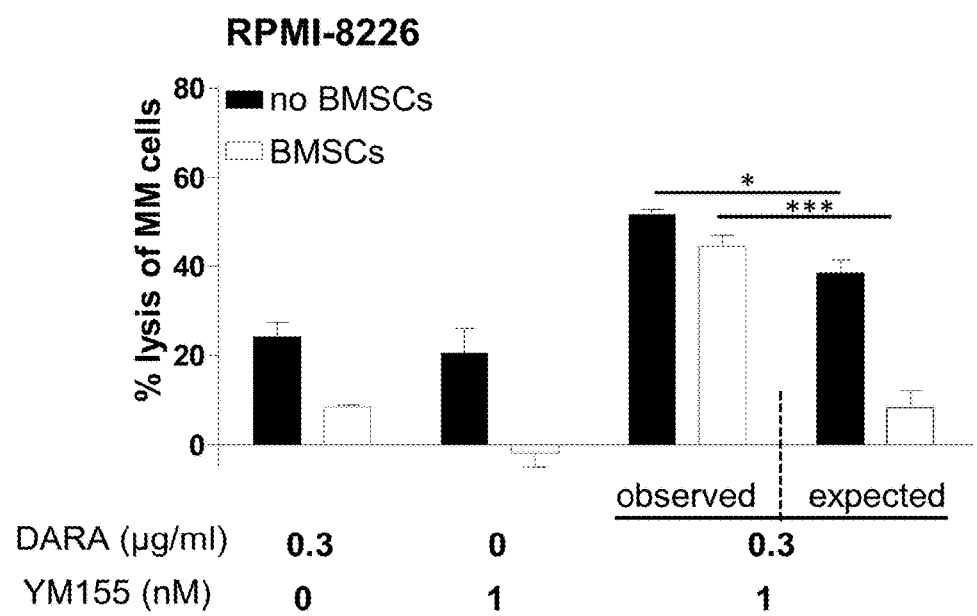
FIG. 4A. Daratumumab in combination with YM155 provide synergistic effect on MM cell killing by ADCC in the presence of stromal cells. Luciferase transduced RPMI8226 MM cells were cultured in presence or absence of HD-BMSCs. Daratumumab and YM155 were added at the indicated concentrations. HD-PBMCs were added in all wells at a PBMC:MM ratio of 40:1 as a source of NK cells to induce ADCC. RPMI8226 cell survival was determined after 4 hours by BLI. The % lysis was calculated relative to the survival of RPMI8226 cells that did not receive any treatment. In the case of the YM155 and daratumumab combination, the expected lysis values were deduced from daratumumab and YM155 treatment alone, assuming that the cumulative effect would be additive, but not synergistic. The statistical differences between the expected and observed results were determined in a paired t test ***=P<0.005, *=P<0.05. DARA: daratumumab.
Figure 4B:
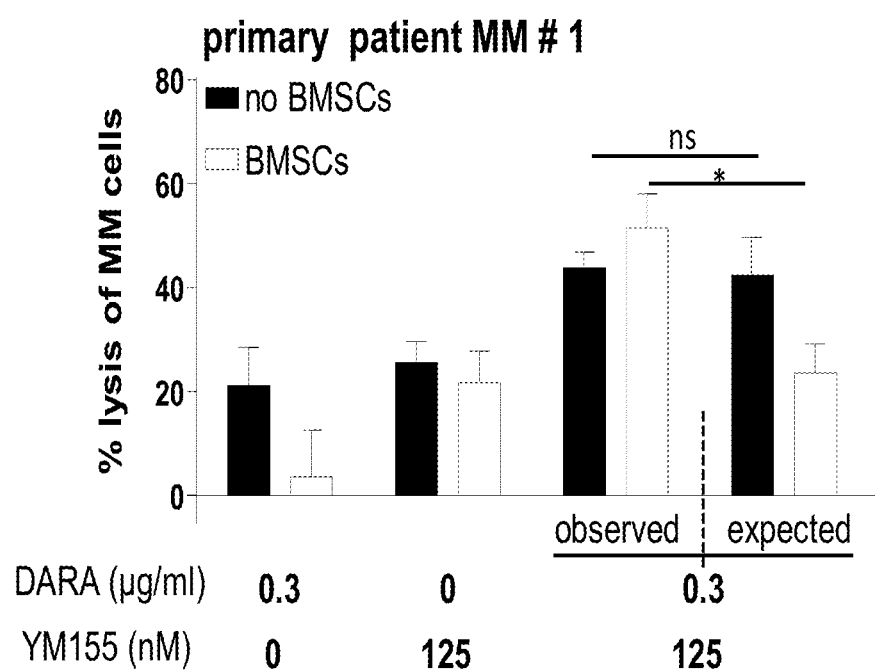
FIG. 4B. Daratumumab in combination with YM155 provides synergistic effect on primary MM cell killing by ADCC in the presence of stromal cells. Full BM aspirates of the MM patient 1 were cultured in the presence or absence of autologous MM-BMSCs. Daratumumab and YM155 were added at the indicated concentrations. Since BM-MNCs contain sufficient NK cells (in both cases, approximately at a 30:1 NK: MM cell ratio), no additional effector cells were added. After 24 hours, the viable CD138+ MM cells were enumerated in each condition via flow cytometry. The % lysis was calculated relative to the survival of MM cells in BM-MNCs which were cultured at the same conditions but did not receive any treatment. The statistical differences between the expected and observed results were determined in a paired t test. *=P<0.05.
Figure 4C:
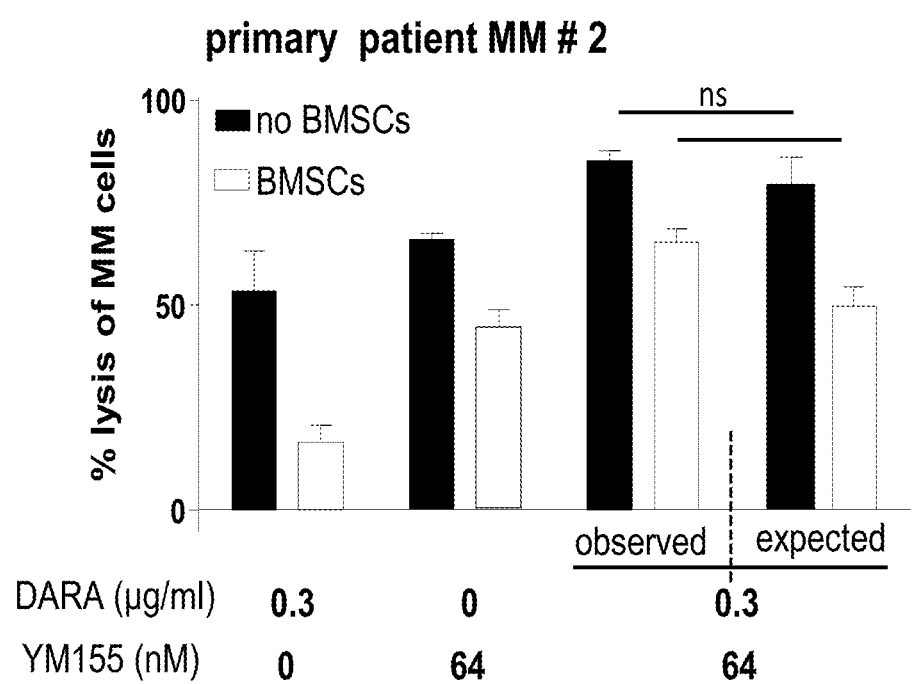
FIG. 4C. Daratumumab in combination with YM155 provides synergistic effect on primary MM cell killing by ADCC in the presence of stromal cells. Full BM aspirates of the MM patient 2 were cultured in the presence or absence of autologous MM-BMSCs. Daratumumab and YM155 were added at the indicated concentrations. Since BM-MNCs contain sufficient NK cells (in both cases, approximately at a 30:1 NK: MM cell ratio), no additional effector cells were added. After 24 hours, the viable CD138+ MM cells were enumerated in each condition via flow cytometry. The % lysis was calculated relative to the survival of MM cells in BM-MNCs which were cultured at the same conditions but did not receive any treatment. The statistical differences between the expected and observed results were determined in a paired t test. *=P<0.05.
Figure 4D:
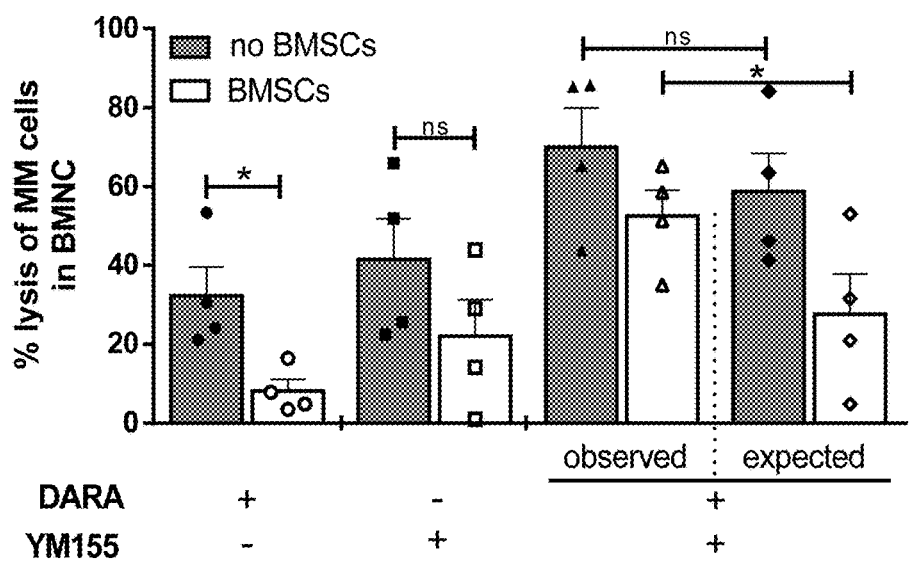
FIG. 4D. Daratumumab in combination with YM155 provides synergistic effect on primary MM cell killing by ADCC in the presence of stromal cells. Bone marrow mononuclear cells (BM-MNCs) from four MM patients containing CD138+ MM cells (45%, 5.5% 10.2% 21.6% for patient 1-4, respectively) were cultured in the presence or absence of autologous MM-BMSCs. Daratumumab (1 ng/ml) and appropriate sub maximal concentrations of YM155 (125, 62, 75 and 50 ng/ml for patient 1-4, respectively) were added. Since BM-MNCs contained sufficient NK cells (7.9%, 7.9%, 10.3% and 9.5% respectively), no additional effector cells were added. After 24 hours, the viable CD138+ MM cells were enumerated in each condition via flow cytometry. The % lysis was calculated relative to the survival of MM cells in BM-MNCs which were cultured at the same conditions but did not receive any treatment. The statistical differences between the expected and observed results were determined in a paired t test. *=P<0.05. ns: not significant. DARA: daratumumab.

In RPMI-8226 cells, daratumumab alone or YM155 alone induced lysis of about 20% of cells in the absence of BMSCs. In the presence of BMSCs, daratumumab induced lysis of about 10% of cells, whereas YM155 had no effect. Combination of daratumumab and YM155 provided a synergistic effect inducing lysis of about 50% of cells in the absence of BMSCs, and inducing lysis of about 45% of cells in the presence of BMSCs (FIG. 4A). The synergistic effect of the combination of daratumumab and YM155 in the BMSCs was about 5-fold. Similarly, the combination of daratumumab and YM155 provided a synergistic effect in the MM patient sample 1 using 120 nM YM155 (FIG. 4B), a moderate synergistic effect in the MM patient sample 2 using a lower amount of YM155 (64 nM) (FIG. 4C), and in a combined sample of MM cells derived from 4 patients (FIG. 4D). YM155 therefore abrogated the protective effects of BMSCs on daratumumab-mediated ADCC in MM cells and cell lines.

Thus, survivin up-regulation may be an important mechanism of suppression of ADCC-mediated killing of MM cells, which can be prevented by pharmacological modulation of survivin.

EXAMPLE 4

In vivo antitumor effect of daratumumab and YM155 combination therapy

Figure 5:
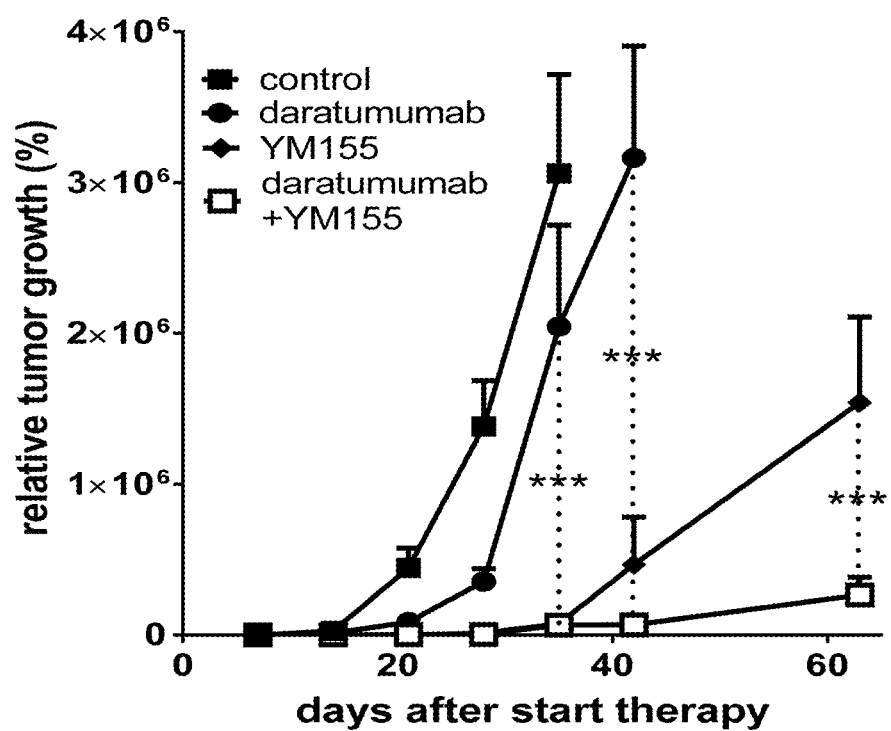
FIG. 5. Antitumor effect of daratumumab and YM155 combination therapy. Analysis of tumor load per treatment group in $RAG2^{-/-}\gamma c^{--}$ mice implanted with UM9 cells. Hybrid scaffolds coated with human MSCs and loaded with luciferase transduced MM cell line UM9 were implanted subcutaneously in the back of $RAG2^{-/-}\gamma c^{--}$ mice (4 scaffolds per mice). Ten days after implantation, the growing tumors were visualized and quantified by BLI. Different groups of mice (n=4) were then either treated with vehicle control (control) or treated with daratumumab, YM155 or daratumumab plus YM155 as indicated. YM155 (or its vehicle, PBS) was delivered with subcutaneous infusion pumps at a rate of 1 mg/kg/d YM155 for 10 days. Each mouse, including those in the control group, received T cell depleted HD-PBMCs ($5\times10^6$ cells) as a source of human NK cells to induce ADCC. Mice were monitored weekly by BLI. Results are expressed as the mean tumor load in each scaffold. The error bars represent the SEM. The statistical differences between mice treated with daratumumab and mice treated with daratumumab plus YM155 were calculated using the Mann-Whitney U-test.
*** P<0.001.

The in vivo relevance of the combination of daratumumab with YM155 was tested in the preclinical xenograft model in $RAG2^{-/-}gc^{-/-}$ mice, in which MM tumors were grown in a humanized BM-like niche created by subcutaneous implantation of ceramic scaffolds coated with human BMSCs. Hybrid scaffolds coated with human MSCs and loaded with luciferase transduced MM cell line UM9 were implanted subcutaneously on the back of $RAG2^{-/-}\gamma c^{-/-}$ mice (4 scaffolds per mice). Ten days after implantation, the growing tumors were visualized and quantified by BLI. Different groups of mice (n=4) were then either treated with vehicle control (control) or treated with daratumumab, YM155 or daratumumab plus YM155. YM155 or its vehicle, PBS was delivered with subcutaneous infusion pumps at a rate of 1 mg/kg/d YM155 for 10 days. Each mouse, including the control group, received T cell-depleted HD-PBMCs ($5 \times 10^6$ cells) as a source of human NK cells to induce ADCC. Mice were monitored weekly by BLI. FIG. 5 shows the relative tumor growth for each group. Statistical differences between mice treated with daratumumab and mice treated with daratumumab plus YM155 were calculated using the Mann-Whitney U-test. Daratumumab had a marginal effect on tumor growth. The anti-MM effect was more pronounced with YM155, which furthermore showed strong synergism with daratumumab to achieve significantly improved anti-MM effects. These results suggested that a clinical benefit may be expected from the combination of daratumumab with the survivin inhibitor YM155.

The results presented demonstrate that suppressing survivin levels with a small molecule YM155 not only improved daratumumab-mediated ADCC in the absence of BMSCs, but importantly abrogated the ADCC resistance induced by BMSCs. The addition of YM155 to daratumumab demonstrated enhanced antitumor effects also in the absence of BMSCs, which suggest the potential benefits of YM155-daratumumab combination therapy even if the MM cells are not in direct contact with BMSCs, such as in plasma cell leukemia. Moreover, the significant improvement of ADCC, up to a four-fold improvement of MM cell lysis, in the presence of BMSCs, suggests that a larger benefit from combining daratumumab therapy with YM155 can be achieved for MM cells which reside in the BM. It was also demonstrated that YM155 treatment does not negatively interfere with NK cell functions or viability, which is a prerequisite to consider clinical application of this combination therapy.

The efficacy of daratumumab in combination with YM155 was demonstrated in multiple myeloma, however, it can be extrapolated that the combination therapy may also be beneficial for other hematological tumors that express CD38, especially for those that mainly reside in the BM. In this respect AML is an eminent candidate, since AML cells not only express high levels of CD38, but also high levels of survivin, which is a predictor for poor clinical outcome. Another potential candidate for combination therapy might be CLL, since CLL cells have high survivin expression in the BM and CD38 is expressed in some patients. High CD38 and survivin expression in about 50% of non-Hodgkin lymphomas, makes this disease also relevant for evaluation of the efficacy of YM155-daratumumab combination. Altogether, a combination of daratumumab and YM155 may be broadly applicable for a wide range of hematological tumors.

We claim:

1. A method of treating a subject having multiple myeloma (MM), comprising administering to the subject in need thereof an anti-CD38 antibody and a survivin inhibitor for a time sufficient to treat the MM, wherein the anti-CD38 antibody comprises a heavy chain complementarity determining region (HCDR) 1, HCDR2 and a HCDR3 of SEQ ID NOs: 6, 7 and 8, respectively, and a light chain complementarity determining region (LCDR) 1, a LCDR2 and a LCDR3 of SEQ ID NOs: 9, 10 and 11, respectively, and is an IgG1 isotype, and wherein the survivin inhibitor is YM155.

2. The method of claim 1, wherein the anti-CD38 comprises a heavy chain variable region (VH) of SEQ ID NO: 4 and a light chain variable region (VL) of SEQ ID NO:5.

3. The method of claim 1, wherein the anti-CD38 antibody induces CD38-positive cell killing by antibody-dependent cellular cytotoxicity (ADCC), antibody-dependent cellular phagocytosis (ADCP), complement-dependent cytotoxicity (CDC) or apoptosis.

4. The method of claim 1, wherein the anti-CD38 antibody and the survivin inhibitor are administered simultaneously, sequentially or separately.

5. The method of claim 4, wherein the anti-CD38 antibody is administered intravenously.

6. The method of claim 1, wherein the anti-CD38 antibody comprises a heavy chain of SEQ ID NO: 12 and a light chain of SEQ ID NO: 13.

* * * * *

UNITED STATES PATENT AND TRADEMARK OFFICE
CERTIFICATE OF CORRECTION

PATENT NO. : 10,668,149 B2
APPLICATION NO. : 15/189577
DATED : June 2, 2020
INVENTOR(S) : Parul Doshi, Henk M. Lokhorst and Tuna Mutis Page 1 of 1

It is certified that error appears in the above-identified patent and that said Letters Patent is hereby corrected as shown below:

In the Claims

Column 49, Claim 2, Line 59, please insert --antibody-- after "anti-CD38".

Signed and Sealed this
Twenty-eighth Day of July, 2020

Andrei Iancu
*Director of the United States Patent and Trademark Office*

SEQUENCE LISTING

```
<160> NUMBER OF SEQ ID NOS: 23

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45
```

-continued

Gln Trp Ser Gly Pro Gly Thr Thr Lys Arg Phe Pro Glu Thr Val Leu
 50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
             85                  90                  95

His Pro Cys Asn Ile Thr Glu Glu Asp Tyr Gln Pro Leu Met Lys Leu
        100                 105                 110

Gly Thr Gln Thr Val Pro Cys Asn Lys Ile Leu Leu Trp Ser Arg Ile
    115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: antibody VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: antibody VL

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: Antibody HCDR1

<400> SEQUENCE: 6

Ser Phe Ala Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: Antibody HCDR2

<400> SEQUENCE: 7

Ala Ile Ser Gly Ser Gly Gly Thr Tyr Tyr Ala Asp Ser Val Lys
1               5                   10                  15

Gly

<210> SEQ ID NO 8
<211> LENGTH: 13
<212> TYPE: PRT
<213> ORGANISM: Artificial Sequence
<220> FEATURE:
<223> OTHER INFORMATION: mAb HCDR3

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Antibody LCDR1

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Antibody LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Antibody LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: Antibody HC

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 214

```
<212> TYPE: PRT
<213> ORGANISM: Artificial Sequence
<220> FEATURE:
<223> OTHER INFORMATION: Antibody LC

<400> SEQUENCE: 13
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 14
<211> LENGTH: 122
<212> TYPE: PRT
<213> ORGANISM: Artificial Sequence
<220> FEATURE:
<223> OTHER INFORMATION: mAb 003 VH

<400> SEQUENCE: 14
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

```
Gly Thr Leu Val Thr Val Ser Ser Ala Ser
        115                 120
```

<210> SEQ ID NO 15
<211> LENGTH: 107
<212> TYPE: PRT
<213> ORGANISM: Artificial Sequence
<220> FEATURE:
<223> OTHER INFORMATION: mAb 003 VL

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
        100                 105
```

<210> SEQ ID NO 16
<211> LENGTH: 122
<212> TYPE: PRT
<213> ORGANISM: Artificial Sequence
<220> FEATURE:
<223> OTHER INFORMATION: mAb 024 Vh

<400> SEQUENCE: 16

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120
```

<210> SEQ ID NO 17
<211> LENGTH: 107
<212> TYPE: PRT
<213> ORGANISM: Artificial Sequence
<220> FEATURE:
<223> OTHER INFORMATION: mAb 024 VL

<400> SEQUENCE: 17

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 18
<211> LENGTH: 120
<212> TYPE: PRT
<213> ORGANISM: Artificial Sequence
<220> FEATURE:
<223> OTHER INFORMATION: MOR202VH

<400> SEQUENCE: 18

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Tyr Met Asn Trp Val Arg Gln Ala Pro Gly Lys Gly Leu Glu Trp Val
            35                  40                  45

Ser Gly Ile Ser Gly Asp Pro Ser Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
            115                 120
```

<210> SEQ ID NO 19
<211> LENGTH: 109
<212> TYPE: PRT
<213> ORGANISM: Artificial Sequence
<220> FEATURE:
<223> OTHER INFORMATION: MOR202VL

<400> SEQUENCE: 19

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg His Tyr Tyr Val
                20                  25                  30

Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80
```

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
                100                 105

<210> SEQ ID NO 20
<211> LENGTH: 120
<212> TYPE: PRT
<213> ORGANISM: Artificial Sequence
<220> FEATURE:
<223> OTHER INFORMATION: Isatuximab VH

<400> SEQUENCE: 20

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
        50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser
            115                 120

<210> SEQ ID NO 21
<211> LENGTH: 107
<212> TYPE: PRT
<213> ORGANISM: Artificial Sequence
<220> FEATURE:
<223> OTHER INFORMATION: Isatuximab VL

<400> SEQUENCE: 21

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30

Val Ala Trp Tyr Gln Lys Pro Gly Gln Ser Pro Arg Arg Leu Ile
            35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys
                100                 105

<210> SEQ ID NO 22
<211> LENGTH: 142
<212> TYPE: PRT
<213> ORGANISM: hOMO SAPIENS

<400> SEQUENCE: 22

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Cys Phe Lys Glu Leu
    50                  55                  60

Glu Gly Trp Glu Pro Asp Asp Pro Ile Glu His Lys Lys His
65              70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
            115                 120                 125

Glu Lys Val Arg Arg Ala Ile Glu Gln Leu Ala Ala Met Asp
    130                 135                 140

<210> SEQ ID NO 23
<211> LENGTH: 509
<212> TYPE: PRT
<213> ORGANISM: Homo sapiens

<400> SEQUENCE: 23

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65              70                  75                  80

Ile Asn Ala Thr Gly Gln Gly Val Thr Ile Phe Tyr Val Asp Arg Leu
            85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145             150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
```

-continued

```
            225                 230                 235                 240
Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
                275                 280                 285

Ser Lys Ile Pro Asp Ala Lys Ser Pro Leu Pro Val Phe Ala Tyr Thr
                290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
                340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
                370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
                450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500                 505
```